United States Patent
Abedi et al.

(10) Patent No.: US 9,681,492 B2
(45) Date of Patent: Jun. 13, 2017

(54) IMPROVEMENTS WIRELESS SENSOR NETWORKS

(75) Inventors: Saied Abedi, Reading (GB); Hind Chebbo, Cowley (GB)

(73) Assignee: FUJITSU LIMITED, Kawasaki-Shi (JP)

( * ) Notice: Subject to any disclaimer, the term of this patent is extended or adjusted under 35 U.S.C. 154(b) by 1256 days.

(21) Appl. No.: 13/254,069

(22) PCT Filed: Feb. 4, 2010

(86) PCT No.: PCT/GB2010/050174
§ 371 (c)(1),
(2), (4) Date: Dec. 16, 2011

(87) PCT Pub. No.: WO2010/100446
PCT Pub. Date: Sep. 10, 2010

(65) Prior Publication Data
US 2012/0082036 A1    Apr. 5, 2012

(30) Foreign Application Priority Data

Mar. 4, 2009  (EP) .................................... 09154329

(51) Int. Cl.
*H04L 12/26* (2006.01)
*H04W 84/18* (2009.01)
(Continued)

(52) U.S. Cl.
CPC ........ *H04W 84/18* (2013.01); *G06F 19/3418* (2013.01); *G06F 19/3406* (2013.01); *H04W 72/10* (2013.01); *H04W 72/12* (2013.01)

(58) Field of Classification Search
USPC ................................................ 370/241, 329
See application file for complete search history.

(56) References Cited

U.S. PATENT DOCUMENTS

2005/0141451 A1    6/2005  Yoon et al.
2007/0064949 A1*   3/2007  Choi .................... H04B 7/0619
                                                    380/270
(Continued)

FOREIGN PATENT DOCUMENTS

CN    101369996    2/2009
JP    2005-198305  7/2005
(Continued)

OTHER PUBLICATIONS

IEEE Std 802.15.3-2003, Part 15.3: Wireless Medium Access Control (MAC) and Physical Layer (PHY) Specification for High Rate Wireless Personal Area Network (WPANS), by IEEE Computer Society, dated Sep. 29, 2003.*
(Continued)

*Primary Examiner* — Chirag Shah
*Assistant Examiner* — Majid Esmaeilian
(74) *Attorney, Agent, or Firm* — Staas & Halsey LLP

(57) ABSTRACT

A method of allocating resources in a wireless sensor network, the network having functions including medical monitoring of a patient using multiple network devices having sensors, the method including steps of: sensing, by a network device in the network, a life parameter of the patient; recognizing the existence of an emergency condition with respect to the parameter; the network device sending a request for streaming towards a coordinator of the network; the coordinator receiving (S12) the request along with any other requests from other devices in the network; and the coordinator granting (S14, S16) each the request by scheduling one of: a streaming allocation with highest priority for a network device which is in an emergency condition; a streaming allocation of medium priority for a network device sensing a life parameter which is not in an emergency condition; and a streaming allocation of lowest priority for
(Continued)

a network device which is not sensing any life parameter of the patient and which is not in an emergency condition. The emergency condition may be defined with respect to one or more medical parameters of the patient. The method may be applied, for example, to monitoring of patients in a hospital using MBANs operating in accordance with IEEE 802.15.6.

8 Claims, 19 Drawing Sheets

(51) Int. Cl.
    *H04W 72/10*     (2009.01)
    *H04W 72/12*     (2009.01)
    *G06F 19/00*     (2011.01)

(56) References Cited

U.S. PATENT DOCUMENTS

| | | |
|---|---|---|
| 2007/0073861 A1 | 3/2007 | Amanuddin et al. |
| 2009/0023391 A1* | 1/2009 | Falck .......... A61B 5/0024 455/41.2 |
| 2009/0049180 A1 | 2/2009 | Ei et al. |
| 2009/0185548 A1* | 7/2009 | Pratapagiri .......... A61B 5/0002 370/346 |
| 2010/0188988 A1 | 7/2010 | Mulligan et al. |
| 2010/0202354 A1* | 8/2010 | Ho .......................... 370/328 |

FOREIGN PATENT DOCUMENTS

| | | |
|---|---|---|
| JP | 2008-517563 | 5/2008 |
| JP | 2009-507441 | 2/2009 |
| WO | WO2007/083586 A1 | 7/2007 |
| WO | 2009/024925 | 2/2009 |
| WO | WO2009/024925 A2 | 2/2009 |

OTHER PUBLICATIONS

Sana Ullah, et al., "MAC Hurdles in Body Sensor Networks," ICACT, Feb. 15-18, 2009, pp. 1151-1155.
IEEE 802.15.4-2006 Standard, Sep. 8, 2003.
IEEE 802.15.3-2003 Standard, Sep. 29, 2003.
IEEE 802.15.6 Standard, Jun. 2011.
European Search Report issued Sep. 2, 2009 in European Application No. 09154329.8-1249.
International Search Report issued May 7, 2010 in PCT/GB2010/050174.
Japanese Office Action mailed Jun. 4, 2013 in corresponding Japanese Application No. 2011-552511.
Sana Ullah et al., "MAC Hurdles in Body Sensor Networks", Feb. 15-18, 2009, ICACT 2009, pp. 1151-1155.
Chinese Office Action issued Nov. 21, 2014 in corresponding Chinese Patent Application No. 201080010389.8.

* cited by examiner

| Streaming classes | Medical | Emergency | QoS / Bit Rate |
|---|---|---|---|
| 1 | Yes | Yes | • Lowest delay in response to the required delay<br>• Highest available data rate pipe in response to the required bit rate<br>    Highest streaming priority |
| 2 | No | Yes | • Lowest delay in response to the required delay<br>• Highest available data rate pipe in response to the required bit rate<br>    Highest streaming priority |
| 3 | Yes | No | • Required delay if possible<br>• Required data rate pipe if available<br>    Medium streaming priority |
| 4 | No | No | • Required delay if possible<br>• Required data rate pipe if available<br>    Lowest streaming priority |

*Fig.10*

| Octets: 2 | 1 | 0/2 | 0/2/8 | 0/2 | 0/2/8 | 1 | 0/5/6/10/14 | variable | 2 |
|---|---|---|---|---|---|---|---|---|---|
| Frame Control | Sequence Number | Destination PAN ID | Destination Address | Source PAN ID | Source Address | Stream Index | Auxiliary Security Header | Frame payload | FCS |
| | | | Addressing fields | | | | 52 | | |
| | | | MHR | | | | | MAC payload | MFR |

| Command frame Identifier | Command name | RFD Tx | RFD Rx |
|---|---|---|---|
| 0x01 | Association request | X | |
| 0x02 | Association response | | X |
| 0x03 | Disassociation notification | X | X |
| 0x04 | Data request | X | |
| 0x05 | PAN ID conflict notification | X | |
| 0x06 | Orphan notification | X | |
| 0x07 | Beacon request | | |
| 0x08 | Coordinator realignment | | X |
| 0x09 | GTS request | | |
| 0x0a 0x0b | Reserved Reserved | | |
| 0x0c | Channel time request | X | X |
| 0x0d | Channel time response | X | X |
| 0x0e-0xff | Reserved | | |

IMPROVEMENTS WIRELESS SENSOR NETWORKS

CROSS REFERENCE TO RELATED APPLICATIONS

This application is a national phase application, under 35 U.S.C. 371, of international application No. PCT/GB2010/050174, filed on Feb. 4, 2010, which claimed priority to European Patent Application No. 09154329.8, filed on Mar. 4, 2009, the disclosures of all of which are incorporated herein by reference.

FIELD OF THE INVENTION

The present invention relates to wireless sensor networks and particularly, but not exclusively, to body area networks including wirelessly-communicating sensors disposed on or around, or implanted in, a human or animal body.

BACKGROUND OF THE INVENTION

Wireless sensor networks of various kinds have been proposed recently. In particular, the so-called Body Area Network or BAN is an example of wireless personal area networks (WPANs), used to convey information over relatively short distances.

Unlike wireless local area networks (WLANs), connections effected via WPANs involve little or no infrastructure. This feature allows small, power-efficient, inexpensive solutions to be implemented for a wide range of devices. Of particular interest is the possibility of the medical BAN (MBAN) in which sensors are used to monitor the status of a patient. A BAN employing mainly sensors for feeding sensed data to a data sink is an example of a wireless sensor network (WSN); however, more active devices, such as actuators, may be also be included in a MBAN.

Standard IEEE 802.15.4 defines the physical layer (PHY) and medium access control (MAC) sublayer specifications for low data-rate WPANs. IEEE 802.15.4 has some similarities with a standard for high data-rate WPANs, IEEE 802.15.3. The documents IEEE Std 802.15.4-2006 and IEEE Std 802.15.3-2003 are hereby incorporated by reference in their entirety.

WPANs of the type envisaged in IEEE 802.15.4 are suitable for applications such as industrial monitoring, but do not offer the kind of data reliability required for MBANs, nor do they provide any mechanism for reliably streaming data.

In medical applications, there is a requirement to reduce the costs associated with human labour while increasing the reliability and process automation and reducing human error. Sensors can provide the required intelligence, and already are widely employed in medical equipment. This includes hospital recuperative care, home care, intensive care units and advanced surgical procedures. There are many different types of sensors employed for medical applications, including external sensors for pulse, temperature etc., sensors which come in contact with body fluids, sensors used in catheters (through incision), sensors for external applications, disposable skin patches with wireless sensors, and implantable sensors.

A WPAN of sensors around a patient in a hospital or medical ward could provide multiple clinical benefits including patient mobility, monitoring flexibility, extension of monitoring into care areas that are currently unmonitored, reduced clinical errors and reduced overall monitoring costs.

Body worn sensors may include various sensor types on a single patient body. They require a capability to be applied or removed quickly from the patient's body.

On an individual basis, such sensors may have bit rates of as low as 1-2 kbps per patient and on an aggregate basis they may require a 10 kbps bit rate. A range of as little as a few meters may be adequate. However, medical WSN applications are mission critical applications in the clinical environment. Robust wireless links for bounded data loss and bounded latency, capacity for patient and sensor density, coexistence with other radios, battery life for days of continuous operations and small form factors for body worn devices, are among the requirements for medical WSNs or MBANs. These requirements can be satisfied through utilization of techniques such as diversity and error control techniques in the time and frequency domain, including Forward Error Correction (FEC) and Adaptive Repeat reQuest (ARQ), low duty cycle TDMA for sensor information rate, and more efficient small antennas.

Efforts are therefore in progress to define a further standard IEEE802.15.6 which aims to define the properties of Body Area Networks, particularly for medical applications. One of the key requirements of IEEE802.15.6 is high reliability for medical applications, one aspect of which concerns the streaming of data, such as sensor data, with a certain QoS guarantee so as to ensure reliable reception. This is even more important for emergency situations where the life of the patient depends on the reliability of wireless links in medical WSN applications. Existing standards such as IEEE802.15.4 have been designed for commercial applications with no consideration of such emergency life saving scenarios.

Accordingly, there is a need to provide a streaming mechanism for BANs and to ensure quality-of-service (QoS) of streamed data in a BAN, particularly for medical applications.

SUMMARY OF THE INVENTION

According to a first aspect of the present invention, there is provided a coordinator for use together with other network devices in a wireless sensor network, including:

transceiver means arranged to receive a request for streaming originated by at least one of the network devices; and scheduling means arranged to grant the request by allocation of network resources to an extent determined by conditions in the network, the conditions including whether the network device which originated the request is in an emergency condition.

In this way, in a network of possibly many network devices making competing demands on the available resources, the coordinator is able to give precedence, in granting of streaming requests, to a network device in an emergency condition.

Here, "emergency condition" will usually refer to some parameter of an entity being monitored by the wireless sensor network. For example, where the wireless sensor network is used (partly or exclusively) for medical monitoring, "emergency" can mean some critical condition of a life parameter (medical parameter) of a patient being monitored.

The existence of the emergency condition may be determined either at the originating device itself, or elsewhere in the network (e.g. at the coordinator, or at some higher level including possibly human decision-making). At least in the former case, preferably, the scheduling means is responsive to a declaration of the emergency condition received in the request. That is, for example, the request may include one or more bits for signalling the existence of an emergency state. Such bit(s) may also be used to signal lifting of an emergency condition, when the parameter being sensed is no longer at a critical level. Alternatively the coordinator may become aware of the emergency in another way; for example the coordinator itself may determine existence of the emergency with respect to the network device making the request.

One important potential application of the present invention is to medical monitoring. Thus, the emergency condition may involve a medical emergency in respect of a life parameter of a patient being sensed by a sensor of the network device from which the request originated. Preferably, in this case, the other conditions taken into account by the coordinator include whether or not the network devices making requests are medical devices. However, an emergency condition may also involve other kinds of parameter, as in the case of a fire alarm or security equipment.

In the coordinator, preferably, the scheduling means is arranged to grant the request by scheduling any of the following types:

a streaming allocation with highest priority for a medical device or a non-medical device in an emergency condition;

a streaming allocation of medium priority for a medical device not in an emergency condition; and a streaming allocation of lowest priority for a non-medical device not in emergency.

Here, "priority" of streaming allocation can include determining at least one of a delay time for transmission to or from the network device, the size of a data pipe to or from the network device, and precedence over requests from other network devices.

The coordinator may be used in a frame-based system such as IEEE 802.15.6, and thus arranged for wireless communication with the network devices in units of frames. In such a system, typically all communications including requests for bandwidth are made in frames each having a frame header and frames are time-divisions of a larger superframe. Streams are allocated within a contention-free period of such a superframe. Upon receipt of a frame containing a request by the transceiver means, the scheduling means is responsive to a streaming request included in a frame header.

More particularly, the request may be indicated by setting a stream index to a value reserved for unassigned streams. To grant the request, the scheduling means may set a value of the stream index to indicate the type of streaming allocation being requested and the transceiver means may transmit a frame containing the stream index in its frame header.

Where there are insufficient available resources in the network to grant a new streaming allocation, preferably the scheduling means is further arranged for taking away network resources allocated to an existing stream in the network if necessary to grant the request originated from a network device in an emergency condition. This taking away of network resources may include at least one of reducing an allocation to an existing stream and terminating the existing stream. It may also involve reducing or terminating a plurality of existing streams simultaneously, for example where an MBAN includes various non-medical devices for whom services can be safely curtailed.

On the other hand, an existing emergency condition may be lifted after some time. In this event, preferably, the scheduling means is further arranged to re-allocate, to other network devices, resources which had been allocated to a stream requested by the network device formerly in emergency.

According to a second aspect of the present invention, there is provided a network device for use in a wireless sensor network, comprising:

a sensor for sensing a parameter of an entity monitored by the network;

emergency recognising means for recognising an emergency condition with respect to the parameter; and requesting means responsive to the recognising means recognising an emergency condition to transmit a request for streaming towards a coordinator in the network.

One possibility is for the emergency recognising means itself to detect the existence of the emergency condition from data sensed by the sensor, and at least in this case the request for streaming preferably includes an indication of the emergency condition. Alternatively the emergency recognising means is notified of the emergency condition by the coordinator. In the event that the coordinator is already aware of the emergency condition affecting a given network device there may be no need for the emergency to be indicated explicitly in the request.

Preferably, assuming a frame-based network organised along the lines of IEEE 802.15.4, the requesting means is arranged to transmit the request by transmission of a frame with a frame header containing a stream index set to a pre-arranged value denoting an unassigned stream, and/or by transmission of a MAC command frame in which a command frame identifier signifies a channel time request.

The network device may transmit the request directly to the coordinator, for example in a network having a star topology; alternatively the request may be routed via one or more intermediate network devices such as would occur in a peer-to-per configuration.

According to a third aspect of the present invention, there is provided a wireless sensor network including at least one coordinator as defined above and a plurality of network devices each as defined above. As already mentioned, such a network could be applied to medical monitoring of one or more patients in a medical environment such as a hospital.

In all cases above, the entity being monitored may be a living body (human or animal) but could also be an industrial entity such as a factory or installation. An emergency condition with respect to the wireless device refers to some critical level or range being reached by the parameter for which data is being sensed or recorded using the device; for example, a medical parameter in the case of an MBAN, or alternatively a parameter relating to fire or intrusion detection in the case of a safety or security application.

Also, in the above, a "request for streaming" includes a request to modify an existing stream e.g. by increasing the bit rate.

According to a fourth aspect of the present invention, there is provided a method of allocating resources in a wireless sensor network, the network having functions including medical monitoring of a patient using multiple network devices having sensors, the method including steps of:

sensing, by a network device in the network, a life parameter of the patient;

recognising the existence of an emergency with respect to the parameter;

the network device sending a request for streaming towards a coordinator;

the coordinator receiving the request along with any other requests from other devices in the network; and the coordinator granting each the request by scheduling one of:

a streaming allocation with highest priority for a network device which is in an emergency condition;

a streaming allocation of medium priority for a network device sensing a life parameter which is not in an emergency condition; and a streaming allocation of lowest priority for a network device which is not sensing any life parameter of the patient and which is not in an emergency condition.

Further aspects of the present invention provide software which, when executed by a processor of a coordinator or a network device of a wireless sensor network, provides the coordinator or network device according to the first or second aspect defined above, respectively. Such software may be stored on a computer-readable medium.

BRIEF DESCRIPTION OF THE DRAWINGS

For a better understanding of the present invention, and to show more clearly how it may be carried into effect, reference will now be made, by way of example only, to the following drawings in which:

FIG. 10 is a table for mapping QoS of streaming to types of application and an emergency or non-emergency situation;

FIG. 21 shows a modified frame format proposed for IEEE 802.15.6 in an embodiment of the present invention; and FIG. 22 shows a table of values of a command frame identifier in a MAC command frame modified in accordance with another embodiment of the present invention.

DISCLOSURE OF THE INVENTION

Before explaining the embodiments of the present invention, some background explanation will be given of those parts of IEEE 802.15.4 which are expected to have relevance for the IEEE 802.15.6 standard currently under development, and/or for Body Area Networks including MBANs.

Figure 1:
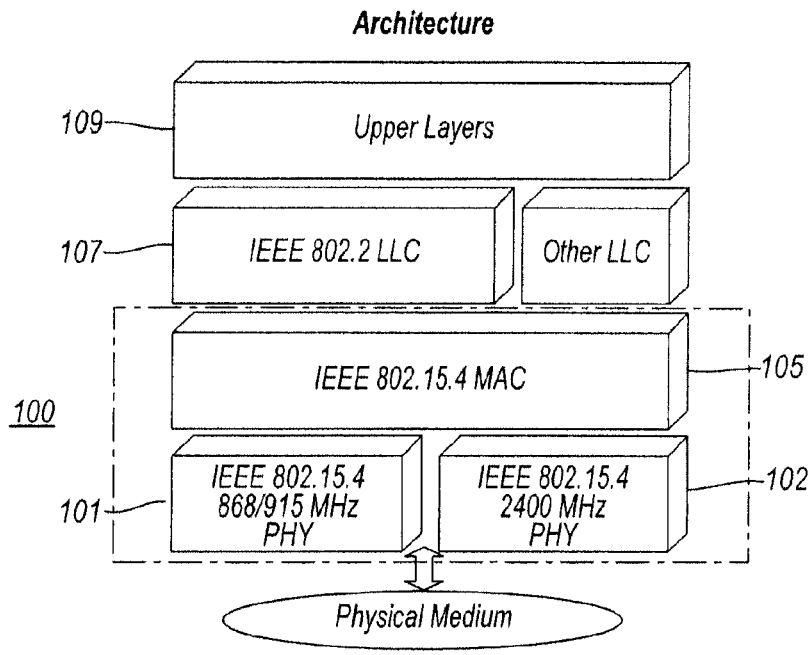
FIG. 1 illustrates protocol layers in an IEEE 802.15.4 WPAN.
Figure 2:
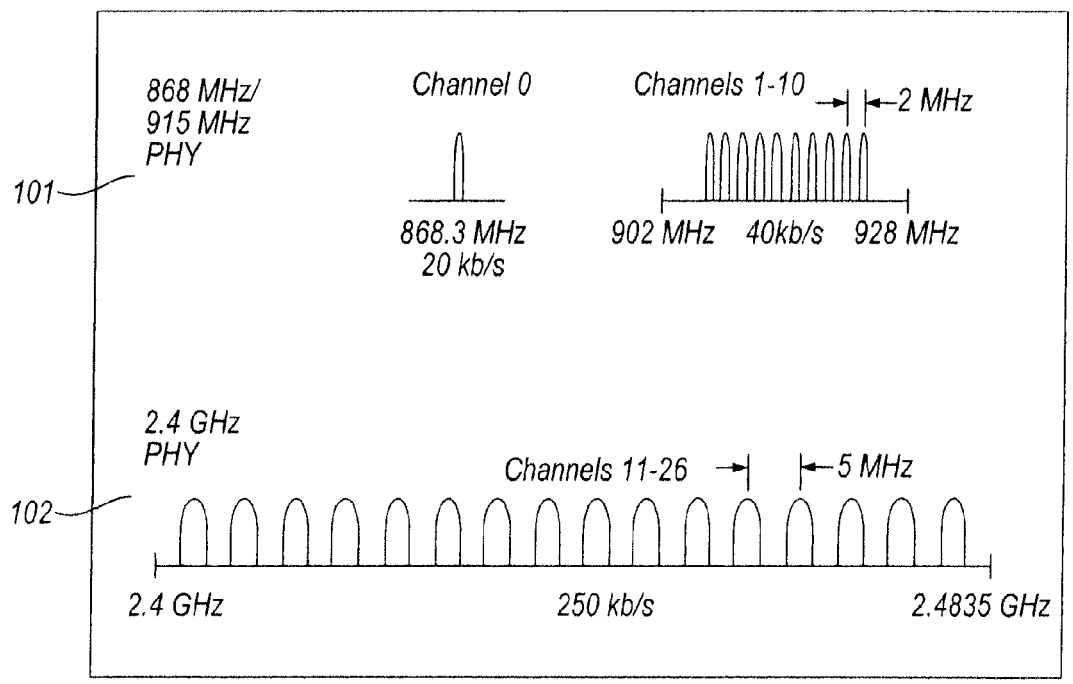
FIG. 2 illustrates possible PHY bands of the IEEE 802.15.4 WPAN.

FIG. 1 shows the general architecture of a IEEE 802.15.4 WPAN, labelled 100, in terms of the layered OSI model, in which the physical medium is accessed via a PHY layer containing the radio transceiver and its low-level control. As shown, there are two alternative frequency bands 101, 102 for the PHY, which are illustrated in FIG. 2. The lower frequency band 101 provides a single 20 kb/s channel centred on 868.3 MHz, and/or ten channels each of 40 kb/s centred on 915 MHz. The higher frequency band 102 provides 16 channels each of 250 kb/s and centred on a frequency of 2.44 GHz. Which of these bands is used will depend on local regulatory requirements.

Access to the PHY is provided by a MAC (Medium Access Control) sublayer indicated by 105 in FIG. 1. Above this, and external to the WPAN 100 as such, are provided a LLC (Link Layer Control) allowing access to the WPAN from other networks; this may be in accordance with the IEEE 802.2 standard, or of another type. Finally, upper layers 109 above the LLC include a network layer to provide network configuration, manipulation, and message routing, and an application layer which provides the intended overall function.

Figure 3:
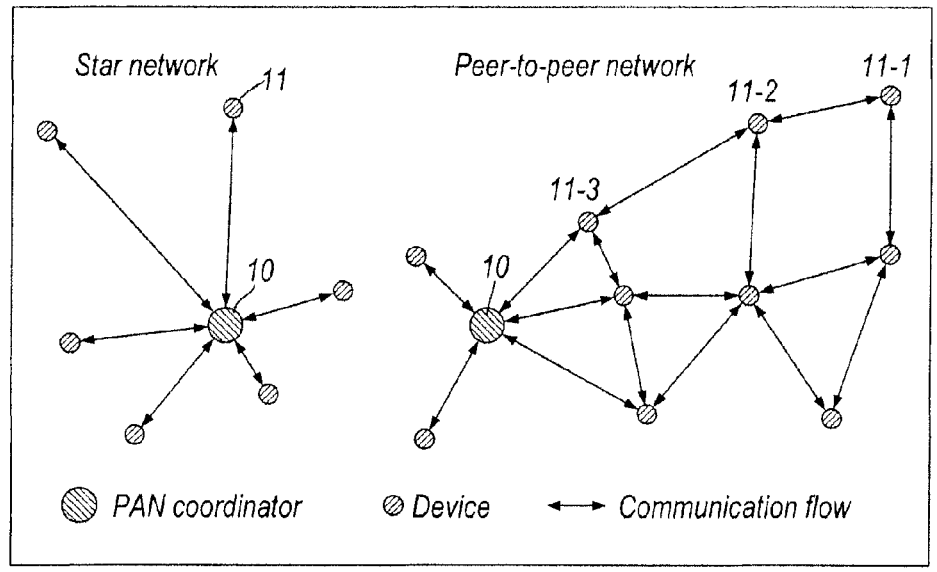
FIG. 3 illustrates Star and Peer-to-Peer topologies of a WPAN.

One task of the MAC sublayer is to control the network topology. Star and peer-to-peer are two known topologies in communications networks, and both are provided for in IEEE 802.15.4. In both cases, the topology distinguishes between two basic kinds of network node: devices and coordinators. As shown in FIG. 3, in the Star topology a number of devices 11 communicate directly with a central coordinator 10; whilst in the peer-to-peer configuration, communications by a device 11-1 with the communicator are made along one or more hops with intermediate devices 11-2 and 11-3 acting as relays. The coordinator acts as the access point to the upper layers; in the case of a WSN, it acts as the sink for the data collected by the sensors. Given that the communication range of each device may be very limited (a few meters), the peer-to-peer topology allows a greater area to be covered. The topology may be dynamic, changing as devices are added or leave the network.

In the case of MBANs, for example, a star network would be appropriate in the situation where a coordinator is provided at each patient site (such as a hospital bed), exchanging signals with devices on a single patient. Peer-to-peer would be a more appropriate topology where one coordinator was provided to serve a number of patients (the coordinator might be located at a fixed point in a hospital ward). Thus, whilst the devices 11 will generally be mobile the coordinator may be either mobile or fixed. Peer-to-peer networks may also be more suited to fast-changing environments where it is required to set up or change the network quickly, or to allow self-organisation and self-healing of the network. Self-healing may include, for example, establishing a new coordinator in the event that an existing coordinator has failed or left the network.

Multiple star and/or peer-to-peer networks may be set up in the same location such as a hospital, each with their own coordinator. In this case it will be necessary for the respective coordinators to collaborate in order to avoid mutual interference and to allow sharing or collation of data. In IEEE 802.15.4 such networks are called clusters, and provision is made for establishing an overall coordinator for the clusters as well as for dividing and merging clusters.

Nodes in a WPAN may be constituted by units of varying capabilities. Generally, the role of coordinator will require a relatively capable apparatus with some processing power and transceiver capable of handling transmissions from multiple sources simultaneously. This in turn will necessitate a sufficient provision of electrical power (in some cases, it may be mains powered). On the other hand, other devices in the network may have more limited processing ability and access only to battery power, and may even be so simple as to be unable to act as a relay hop. Devices with very low power availability may be shut down most of the time and only "wake up" occasionally, for example to transmit sensor data to another node. Thus, the IEEE 802.15.4 standard distinguishes between "full-function" and "reduced function" devices. Availability of power is a particular issue for MBANs in which sensors may be implanted within a body and thus unable to have a large or rechargeable battery.

Two types of WPAN envisaged in IEEE 802.15.4 are beacon-enabled and non beacon-enabled.

Figure 4:
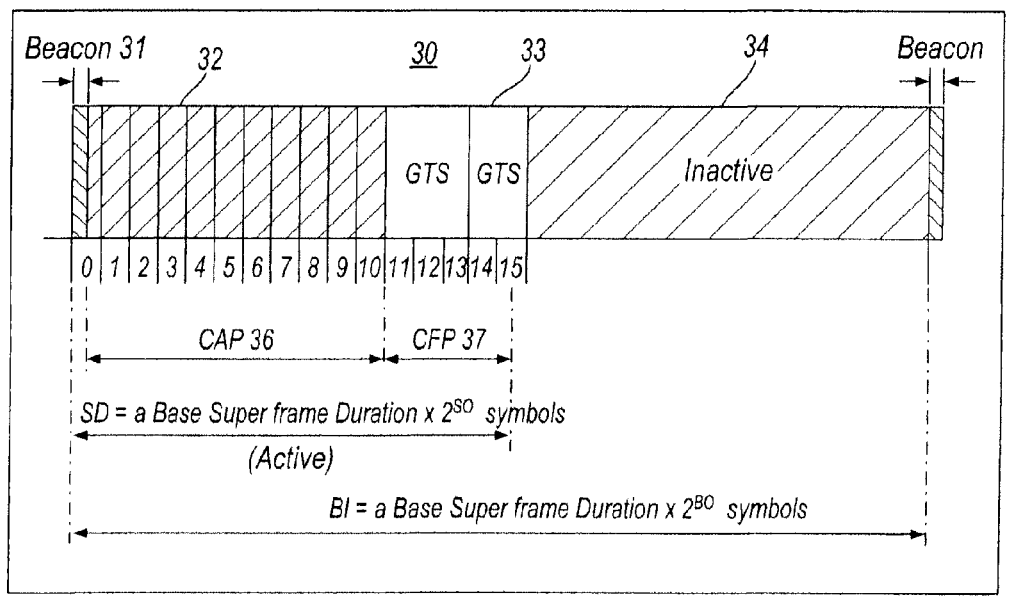
FIG. 4 shows the structure of a superframe in a beacon-enabled IEEE 802.15.4 WPAN.

In a beacon enabled network, the coordinator transmits a beacon periodically and devices listen periodically to that beacon to synchronize to the network and to access the channel. The channel access is in units of "frames" transmitted sequentially within a "superframe" according to a superframe structure as shown in FIG. 4, which is defined by the coordinator. Each superframe 30 consists of two parts: active and inactive. The active part is divided into a contention access period CAP 36, followed by an optional contention free period CFP 37 for guaranteed access; this portion of the superframe is used in embodiments of the present invention for allocation of streams having a quality of service requirement.

As indicated by the vertical divisions in FIG. 4, the superframe is divided into 16 equally-spaced time slots each capable of carrying a frame of data from the coordinator or from a device. Thus, considering the devices associated with one coordinator, only one device may be in communication with the coordinator at a time during each successive time slot within the superframe. First comes a slot 31 for a beacon frame (see below) transmitted by the coordinator. After this, several slots 32 are provided within the CAP, allowing data transmission to or from devices on a contended basis, following the known CSMA-CA algorithm. Briefly, in CSMA-CA, each time a device wishes to transmit within the CAP, it waits for a random period. If the channel is found to be idle, following the random backoff, the device transmits its data. If the channel is found to be busy following the random backoff, the device waits for another random period before trying to access the channel again.

Next there follow the guaranteed time slots GTS 33 of the CFP, and as shown, each of these may extend over more than one basic time slot. After the expiry of the inactive period, the next superframe is marked by the coordinator sending another beacon frame 31. Devices can go to sleep during the inactive period 34 of the superframe. Thus, by extending the length of the inactive period 34, battery power of devices can be conserved as much as possible.

In the non beacon enabled network, the coordinator is not required to transmit a beacon for synchronization unless it is requested to do so (e.g. for network discovery purposes). The channel access is not restricted by the superframe structure and devices are asynchronous, performing all data transfers by CSMA-CA. They can follow their own sleeping pattern according to a certain protocol such as sensor—MAC.

For an MBAN application, the coordinator is external to the body or bodies being monitored. It may be a PDA, a mobile phone, a bedside monitor station or even a sufficiently-capable sensor which on a temporary basis acts as a coordinator. As mentioned above, the coordinator in the beacon enabled network is in charge of providing synchronization and channel access to network devices. The start and end of a superframe is also defined by a coordinator. The coordinator has two main features of potential communications to other networks and access to a sufficient power supply, for example by easy replacement of the charged batteries.

A central care and monitoring unit may also be provided for overall supervision of a network possibly containing several coordinators. This may take the form of a room with monitoring equipments capable of receiving continuous or occasional streams of emergency data from multiple patients. There will typically be nurses or medical specialists stationed in the central unit who are continuously watching and monitoring the patients' data. They will take actions in response to change in patients' conditions. The central care and monitoring unit may be connected wirelessly to the or each coordinator (in which case it may or may not be considered part of the MBAN) or it may have a wired connection to each coordinator (in which case it would normally be considered as outside the MBAN as such).

FIGS. 5 to 8 illustrate data transfers between a device and a coordinator in a IEEE 802.15.4 network. Three basic types of transfer are defined in IEEE 802.15.4:

(i) data transfer to a coordinator as recipient to which a device (sender) transmits its data—used in both star and peer-to-peer topologies;

(ii) data transfer from a coordinator as sender in which the device receives the data—used in both star and peer-to-peer topologies; and (iii) data transfer between two peers—used in peer-to-peer networks only.

Figure 5:
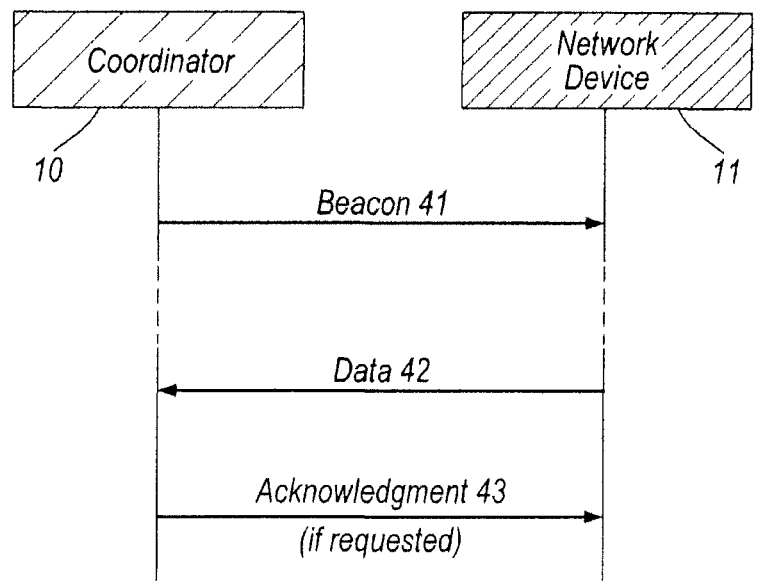
FIGS. 5 to 8 illustrate possible modes of data transfer between a network device and a coordinator in a IEEE 802.15.4 WPAN.
Figure 6:
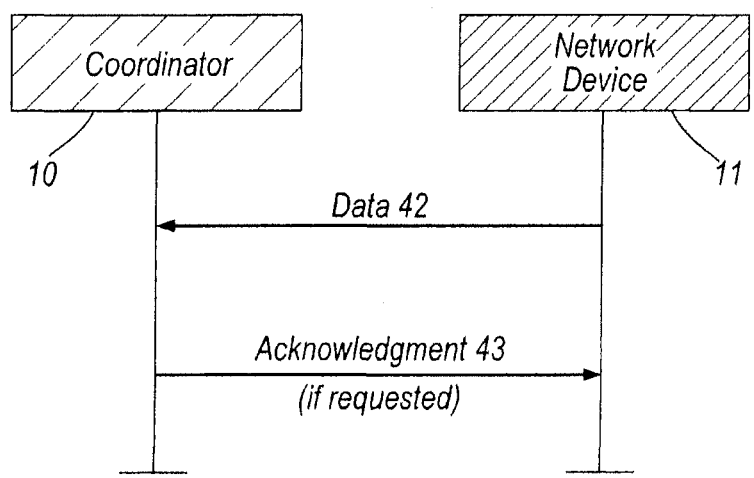

FIGS. 5 and 6 depict a transfer from the device (Network Device 11) and coordinator (Coordinator 10) for both the beacon-enabled and non beacon-enabled case respectively. The difference is that in the beacon-enabled case the device 1 must wait to receive a beacon frame 41 from the coordinator prior to sending the data (data frame 42) using CSMA-CA in the CFP, or using a GTS in the CAP; whilst in the non beacon-enabled case there is normally no beacon frame and the device 11 sends a data frame 42 at will using CSMA-CA. In either case, the coordinator acknowledges the successful reception of the data by transmitting an optional acknowledgment frame or ACK 43. These different types of frame are explained in more detail below.

If the recipient is unable to handle the received data frame for any reason, the message is not acknowledged. If the sender does not receive an acknowledgment after some period, it assumes that the transmission was unsuccessful and retries the frame transmission. If an acknowledgment is still not received after several retries, the sender can choose either to terminate the transaction or to try again. When the acknowledgment is not required, the sender assumes the transmission was successful.

Figure 7:
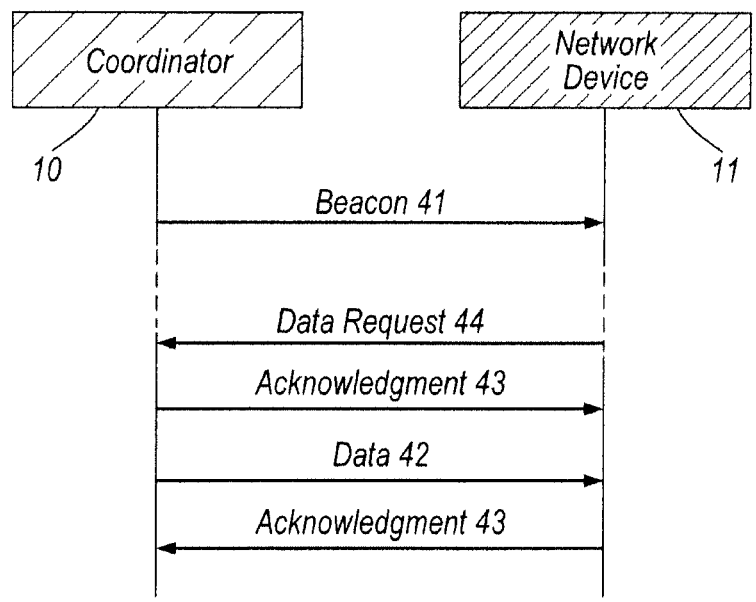
Figure 8:
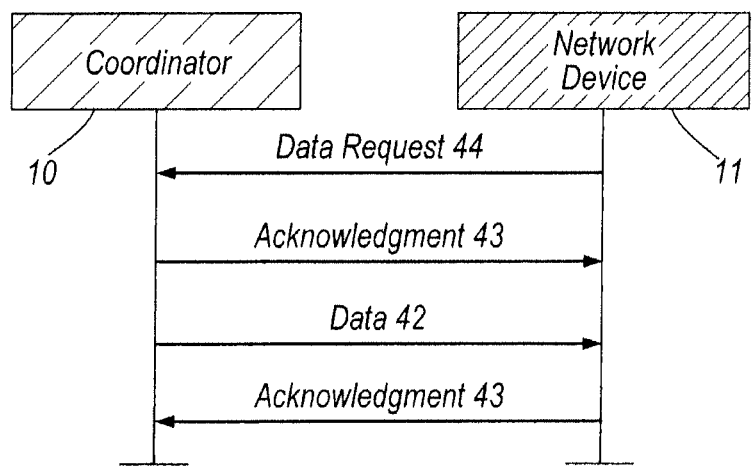

FIGS. 7 and 8 illustrate data transfer from a coordinator 10 to a device 11. When the coordinator wishes to transfer data to a device in a beacon-enabled WPAN (FIG. 7), it indicates in the beacon frame 41 that the data message is pending. The device periodically listens to the beacon frame and, if a message is pending, transmits a data request (MAC command frame) 44 requesting the data by CSMA-CA. The coordinator 10 acknowledges the successful reception of the data request by transmitting an acknowledgment frame 43. The pending data frame 42 is then sent using slotted CSMA-CA or, if possible, immediately after the acknowledgment. The device 11 may acknowledge the successful reception of the data by transmitting an optional acknowledgment frame 43. The transaction is now complete. Upon successful completion of the data transaction, the message is removed from the list of pending messages in the beacon.

In the non beacon-enabled case, the coordinator 10 which has data ready for a particular device 11 has to wait for a data request 44 from the device concerned, sent on a contention basis. Upon receiving such a request, the coordinator sends an acknowledgement frame 43 (this can also be used to signify that no data is ready, if that is the case), followed by the data frame 42, in response to which the device 11 may send another acknowledgement frame 43 in return.

For simplicity, the above procedures have considered only the above cases (i) and (ii) of data transfers between the device and coordinator, but in a peer-to-peer network, as already mentioned, data transfers will generally take place via mechanism (iii), involving one or more intermediate nodes, which increases the risk of collision and the delays involved.

As indicated in FIGS. 5 to 8, communications in a IEEE 802.15.4 network take place in units of frames which divide the available resources in a time-division manner, and which involve frames of four different types:

beacon frame 41, used by a coordinator to transmit beacons data frame 42, used for all transfers of data acknowledgment frame 43, used for confirming successful frame reception MAC command frame 44, used for handling all MAC peer entity control transfers such as data requests.

Figure 9A:
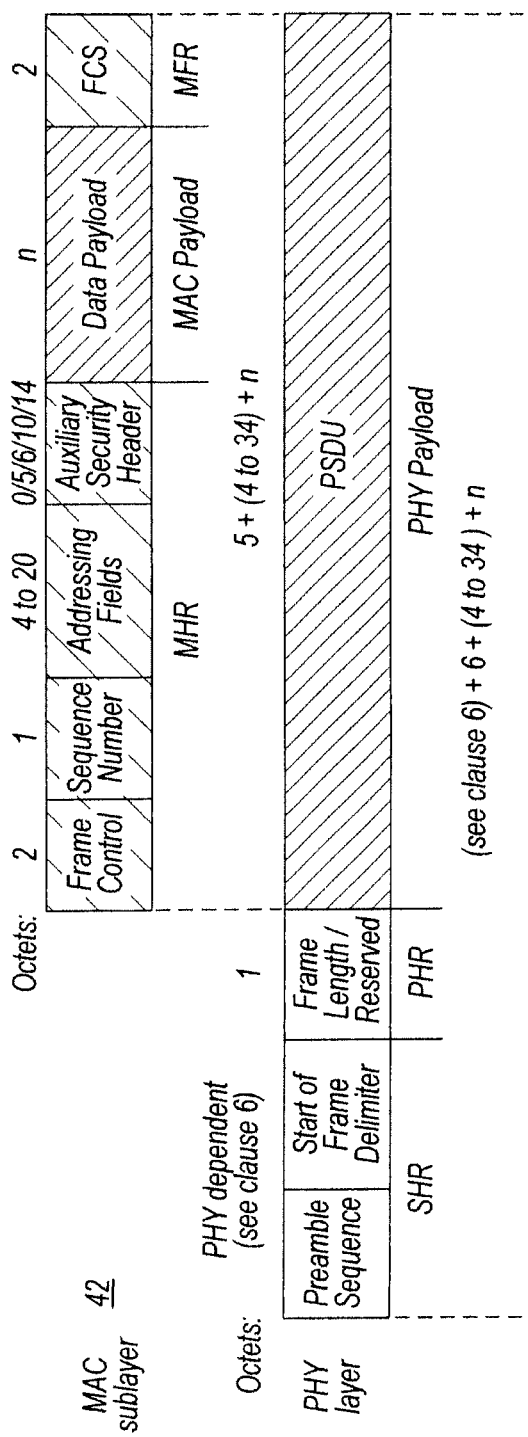
FIG. 9A shows a frame format used for a data frame in a IEEE 802.15.4 WPAN.

The structure of each of the four frame types is quite similar, and is shown in FIG. 9A for a data frame 42 by way of example. In the Figure, the two horizontal bars represent the MAC sublayer and the PHY layer respectively. Time progresses from left to right, and the time length of each successive field of the frame is shown (in octets) above the field concerned. Every frame consists of a sequence of fields in a specific order, these being depicted in the order in which they are transmitted by the PHY, from left to right, where the leftmost bit is transmitted first in time. Bits within each field are numbered from 0 (leftmost and least significant) to k−1 (rightmost and most significant), where the length of the field is k bits.

The data to be sent via the data frame 42 originates from the upper layers. The data payload is passed to the MAC sublayer and is referred to as the MAC service data unit (MSDU). The MAC payload is prefixed with an MAC Header MHR and appended with a MAC Footer MFR. The MAC Header MHR contains a Frame Control field, data sequence number (DSN), addressing fields, and optional auxiliary security header. The MFR is composed of a 16-bit frame check sequence FCS. The MHR, MAC payload, and MFR together form the MAC data frame (i.e., MPDU). The MPDU is passed to the PHY as the PHY service data unit PSDU, which becomes the PHY payload. The PHY payload is prefixed with a synchronisation header SHR, containing a Preamble Sequence and a start-of-frame delimiter SFD, and a PHY header PHR containing the length of the PHY payload in octets. The preamble sequence and the data SFD enable the receiver to achieve symbol synchronization. The SHR, PHR, and PHY payload together form the PHY packet (the PHY protocol data unit PPDU).

The beacon frame 41, acknowledgement frame 43 and MAC command frame 44 have a similar structure, except that the MAC payload has a different function in each case, the acknowledgement frame having no MAC payload. Also, the beacon frame 41, the acknowledgement frame 43 and MAC command frame 44 originate in the MAC sublayer without involvement of the upper layers.

Figure 9B:
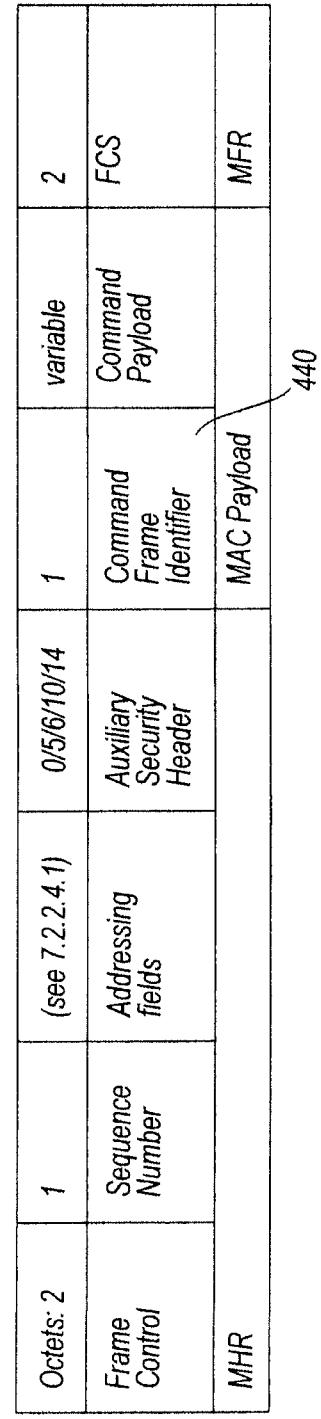
FIG. 9B shows part of a frame format used for a MAC command frame in a IEEE 802.15.4 WPAN.

The MAC command frame 44 is quite similar in structure as shown in FIG. 9B where only the MAC sublayer is depicted. In this case the payload includes a command frame identifier 440 to identify the type of command represented by the MAC command frame.

Although it would be possible, using the above-described data transfer modes, for a network device to send data over a number of superframes so as to achieve a kind of streaming, there is no explicit provision in IEEE 802.15.4 for streaming in which a data transfer persists over several superframes with a certain guaranteed QoS level. However, streaming is provided for in other kinds of communications network including the high-rate WPANs specified by IEEE Std 802.15.3. In general, streams may be "isochronous" (in which transmission occurs periodically, i.e. at some predetermined timing with respect to a known reference such as the start of a superframe) or asynchronous (in which transmission may take place at any time).

Having outlined the background of the present invention, some embodiments will now be described with reference to FIGS. 10 to 21.

Whilst non-streamed transmissions of data in accordance with FIGS. 5 to 8 may be adequate for some WPAN applications, in the MBAN scenario referred to earlier, it would be desirable for medical wireless sensors to be able to stream medical data: in other words, to transmit their sensor data (or possibly receive data/commands from elsewhere) at a more or less steady bit rate over an extended period of time. This is particularly the case given the expected limited storage capability for sensor data of each network device in an MBAN. However, carrying the streaming data within the MBAN considering the limited capabilities of sensor devices requires some changes to the existing standards. Following an IEEE 802.15.4-type superframe structure, only the CFP 37 will be available for streaming. Embodiments of the present invention provide methods to distinguish the medical emergency streaming data from other non-emergency applications, and protocols to achieve the classifications, as well as a new control format suitable for IEEE802.15.6. Embodiments of the present invention further provide methods to schedule the medical streaming data when there are multiple devices involved.

The present invention addresses, for example, the situation in which a patient is being monitored via a MBAN of sensors disposed in, on or around the patient's body. The MBAN may have other uses apart from strictly medical ones (or may be part of a network having such other uses) but it is assumed that at least some of the sensors are involved in sensing one or more parameters, such as heart rate, which might indicate a life-threatening situation for the patient. For example, the sensed parameter may reach a value which exceeds a critical threshold, or fall outside an acceptable range.

It is further assumed that upon recognising such a life threatening situation with respect to at least one sensed parameter, the MBAN (more precisely, the sensor(s) concerned, their coordinator or some higher-level controller), declares an "emergency" state of the sensor(s) monitoring the parameter which is critical. Below, this is referred to as the network device concerned being "in emergency". An "emergency condition with respect to a device" means an emergency with which the device is involved, for example by being a sensor of the parameter which is critical, or by being a coordinator receiving data from such a sensor.

The way in which this emergency state is declared is outside the scope of the present application, but is the subject of a co-pending application by the same applicant. Assuming that there is provision for determining whether devices in a BAN are in emergency or not, it will be desirable to prioritize streaming services to such devices. That is, for any network device in a BAN which is sensing some parameter in an emergency condition, it is desirable to allow this device reliably to stream its sensor data to the coordinator (whether or not it was already transmitting sensor data by streaming or non-streaming techniques).

FIG. 10 shows the classification of streaming applications in association with medical and non-medical devices and their status in terms of being in emergency or not. Here "medical devices" refers to elements of the system, such as sensors for life parameters, which are involved in medical monitoring of a patient. An example of a non-medical device might be an entertainment system for use by patients.

The concept of quality-of service (QoS) is familiar from high-bandwidth wireless communication systems but has not so far been applied to low-rate WPANs and Body Area Networks such as those proposed to be governed by IEEE 802.15.6. In the classification of FIG. 10, four streaming classes 1-4 with three QoS levels are defined: a highest QoS level (Class 1 & 2) for streaming of data from any devices in emergency; a middle level (Class 3) for streaming of data from medical devices not in emergency; and a lowest level (Class 4) for streaming of data from non-medical devices. Note that streaming classes 1 and 2 are equivalent in terms of QoS and bit rate but class 1 (medical emergency) takes priority over non-medical emergency (class2). Class 2 may not be used in some implementations, but in other implementations—perhaps where medical sensing is combined with safety or intrusion monitoring—non-medical devices may also be capable of an emergency state.

Figure 11:
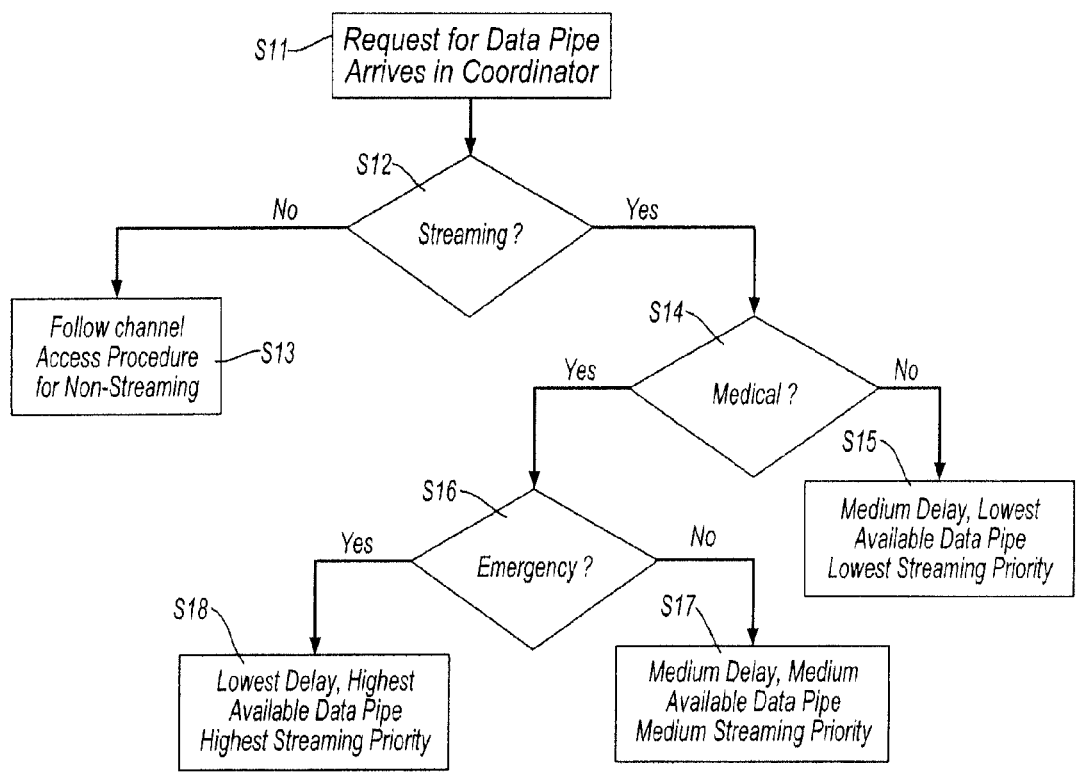
FIG. 11 is a flowchart of steps in a procedure for classifying streaming of data in an embodiment of the present invention.

Using this classification, FIG. 11 shows the scheduling mechanism employed to allocate different streaming bit rates for different applications. In the procedure to be described, it is assumed that a coordinator in a BAN with several network devices takes responsibility for this scheduling task. However, it would be possible for a coordinator to be assisted or instructed in this task by some form of higher level control provided in or for the BAN, such as a central monitoring unit.

The present embodiment employs the concept of a "data pipe" as the conduit for a stream set up between two points in the network, as known to those skilled in the art.

It is assumed first of all that a request for a data pipe, or in other words a request for a certain allocation of resources or slots for data transmission and/or reception, arrives at the coordinator 10 from another network device. (step S11). Note that such a request could be a request for an entirely new stream, or a request to modify a stream already set up. Then (S12) the coordinator decides whether the request is a streaming request (request for persistent allocation of bandwidth such as every superframe), or not. If not (S13) the coordinator follows a procedure to allocate resource to the network device without streaming. If yes (S14) the coordinator next decides whether or not the request is from a medical device. If not (S15) the coordinator sets up a stream using the lowest QoS level shown in FIG. 10. If yes (S16) the coordinator proceeds to consider whether or not the network device is in emergency. The coordinator could be made aware of this in a number of ways, which are outside the scope of the present invention. For example, the frame received from the network device and containing the request for a data pipe could indicate the emergency status using a special emergency frame type. If the network device is not in emergency (S17) the coordinator sets the middle QoS level referred to in FIG. 10. On the other hand if the network device is in emergency then the highest QoS level is set for the data pipe (S18). Thereafter, data is streamed using the pipe; for example, a frame (CTA) may be sent every superframe, or multiple frames may be allocated every superframe, or one frame may be allowed for every n superframes, each frame occupying one or more slots within the CFP 37.

Thus, as shown in the flowchart of FIG. 11 the highest priority is given to a medical device which has an emergency and wants to send streaming data.

The actions of a coordinator 10 in various scenarios for scheduling streams with network devices, according to an embodiment of the present invention, will now be explained by referring to FIGS. 12 to 19.

The resources (wireless bandwidth) available to the coordinator in serving all of its associated network devices can be thought of as providing an overall "data pipe" of fixed size. The size of this data pipe may be determined, for example, by the duration of the CFP 37 of every superframe as already discussed with respect to FIG. 4. That is, isochronous streams can be set up using GTSs within the CFP.

In this embodiment it is assumed that the available streaming data pipe at the coordinator is divided into three major chunks: a data pipe for medical emergency, data pipe for medical non-emergency and data pipe for non-medical applications. Whenever a certain number of medical streaming application devices go into an emergency state, the other two kinds of stream are restricted or interrupted until further notice.

Figure 12:
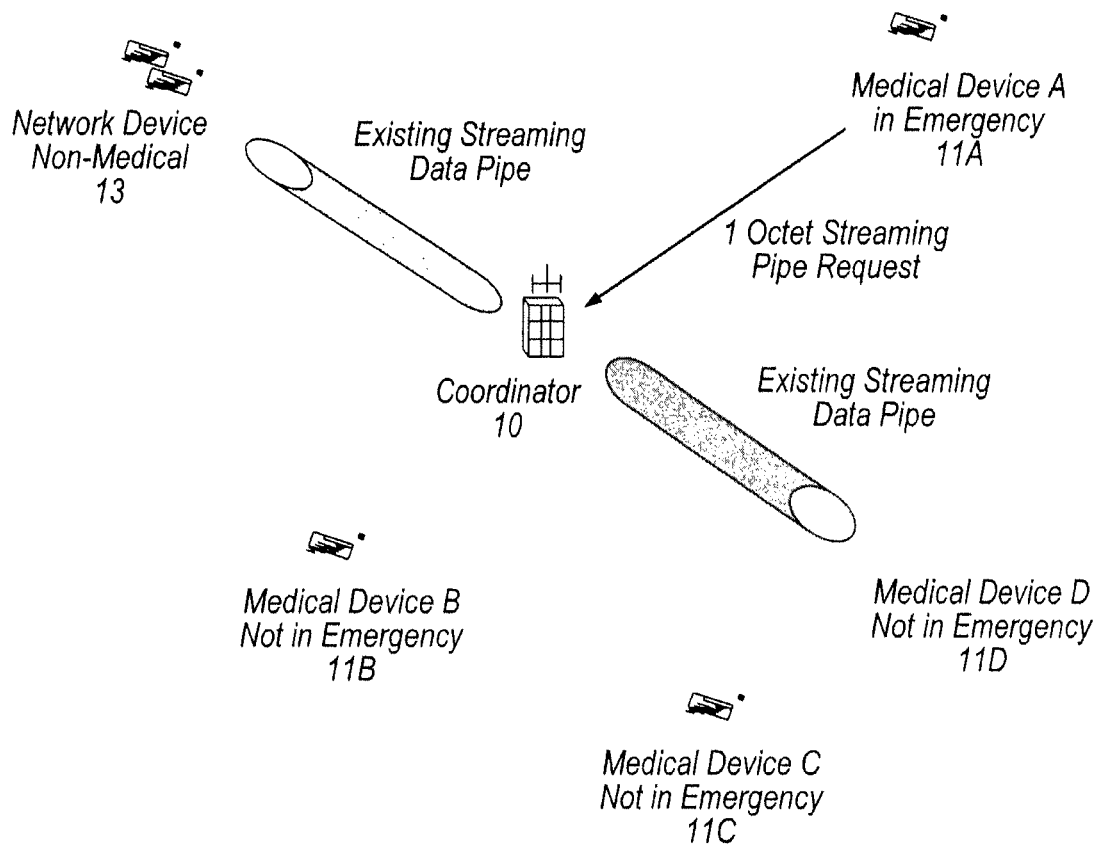
FIGS. 12 to 19 are schematic illustrations of scenarios for allocation of streams among network devices in a BAN.

FIG. 12 shows a typical scenario when the coordinator has managed to coordinate the different devices in terms of their need for streaming according to criticality of their status. That is, a non-medical network device 13 is streaming data to (or from) the coordinator 10 using an existing streaming data pipe (shown in light shading) whilst a medical device 11D not in emergency is streaming via another existing pipe (shown in medium shading). Assume that the coordinator receives a request from medical device 11A currently in emergency, indicating that device 11A needs to stream its sensor data to the coordinator for allowing a given medical parameter to be monitored more closely.

Figure 13:
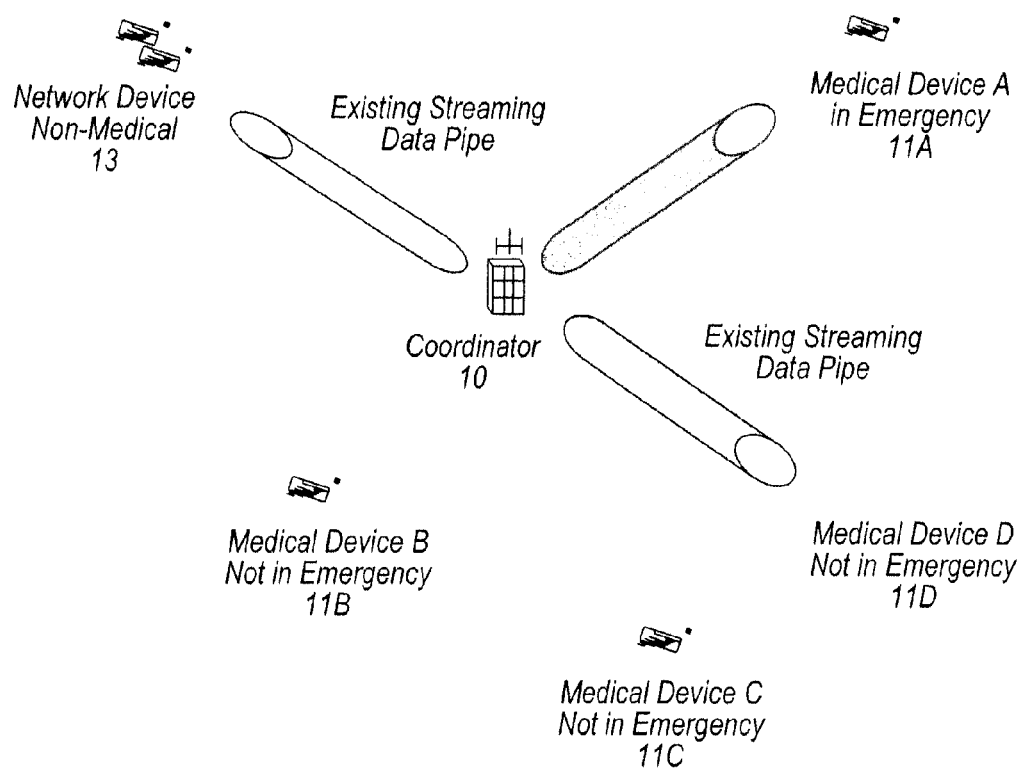

The coordinator 10 considers the remaining data pipe. If the available data pipe is sufficient, the coordinator can allocate the emergency data pipe for network device 11A as shown in FIG. 13 (dark shading). The allocated data pipe is a high priority data pipe compared to other data pipes, and is shown relatively wide indicating a "fat" data pipe with a higher data rate than the other pipes. Device 11A then begins to send sensor data using the data pipe. It may, for example, take advantage of the wide data pipe to take readings more frequently than before and to stream these to the coordinator for allowing close monitoring of a medical parameter.

Note, however, that the network device 11A in emergency may not always need a wide data pipe. Depending on the medical parameter being sensed, there may be only a limited amount of data to stream (e.g. a pulse rate of a patient) and in this case a relatively narrow pipe will suffice. In this instance priority of allocation (ensuring bandwidth is provided every superframe, for example) will be more important than the amount.

Figure 14:
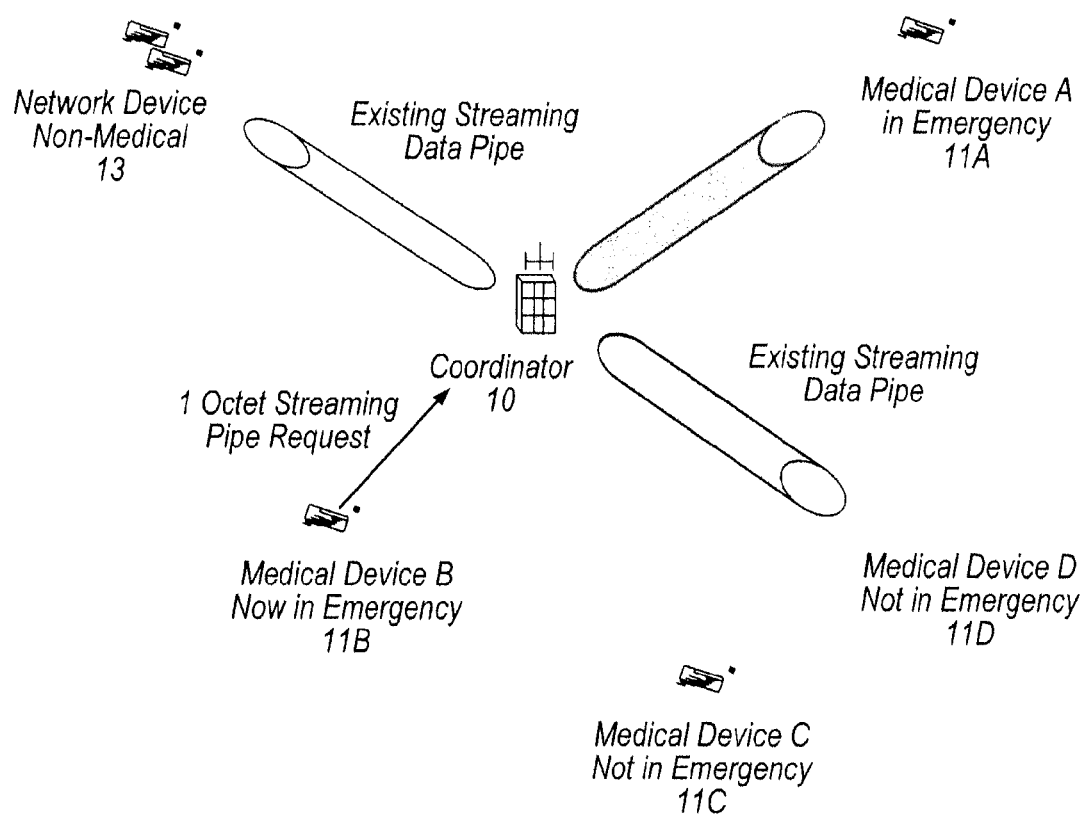

Suppose now that another medical device 11B also goes under (i.e. into) a state of emergency. This could occur, for example, if owing to some deterioration in a patient's condition, a life parameter monitored by medical device 11B becomes critical in addition to the parameter being monitored by medical device 11A. Device 11B sends a streaming request to the coordinator 10 as shown in FIG. 14. The coordinator 10 again evaluates the remaining available streaming pipe which has not been occupied so far by other devices. If sufficient resources are available, the streaming request is simply granted in the same way as in FIG. 13. On the other hand if resources are not sufficient, the coordinator determines which non-medical network devices should stop streaming and give up their data pipe for the sake of the medical device newly in emergency.

Figure 15:
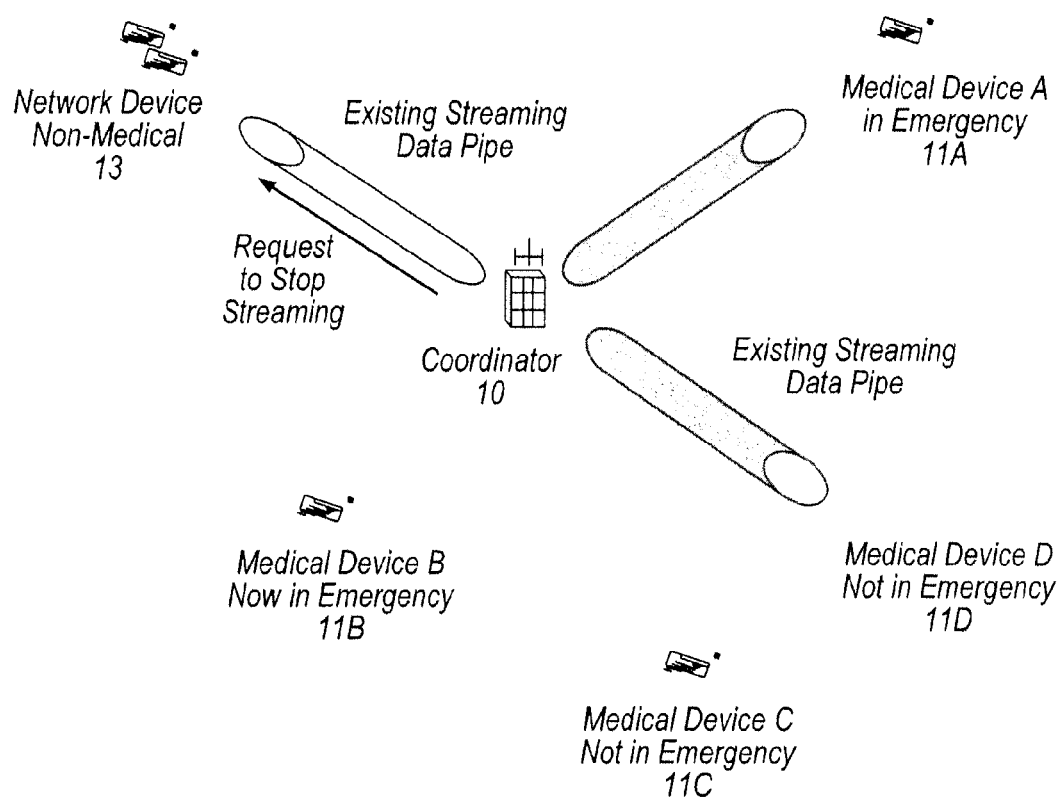
Figure 16:
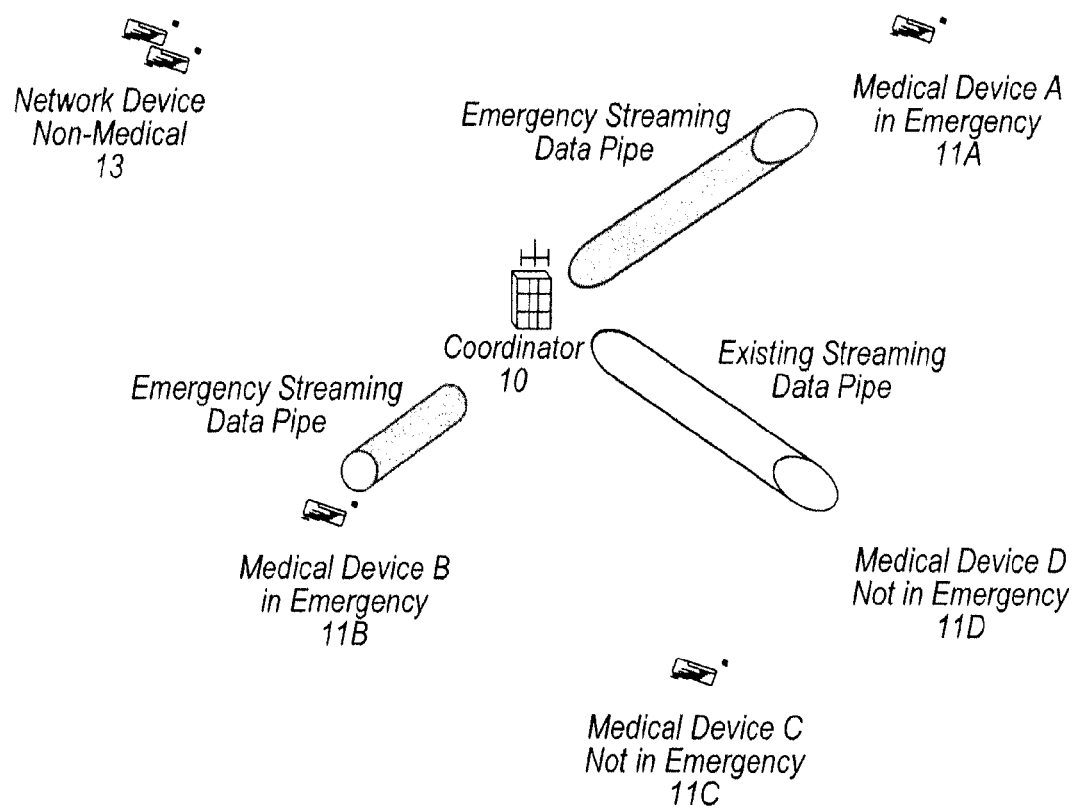

It then sends a signal (control frame) to one or some of the non-medical devices 13 to stop their streaming temporarily as shown in FIG. 15. One or some of the non-medical devices stop their streaming and the pipe is allocated to medical emergency devices as shown in FIG. 16: that is, the light-shaded thin pipe between coordinator 10 and network device 13 shown in FIG. 15 has been replaced by the wider, dark-shaded pipe between coordinator 10 and medical device 11B.

Although the above illustration involved stopping a data pipe for simplicity, it should be noted that resources may also be made available by restricting an existing stream which then continues at a lower bit rate.

In an extreme case, if there are resources in a superframe not allocated to any emergency streaming medical device, but rather allocated to non-medical or non-emergency medical devices, then coordinator might allocate such resources additionally to the medical device in emergency in order to reduce streaming delays. On the other hand there is no need to take resources away from non-emergency applications if the existing allocation to the emergency streaming device already provides an acceptable QoS and delay profile. For example, if an emergency streaming application has a low bit rate (due to the properties of the sensor, for example) and only requires 20% of the data pipe for the required QoS and delay, then there is no need to allocate 50% of the total pipe to this device as this would lead to undesired delays and packet dropping for the non-emergency devices.

Figure 17:
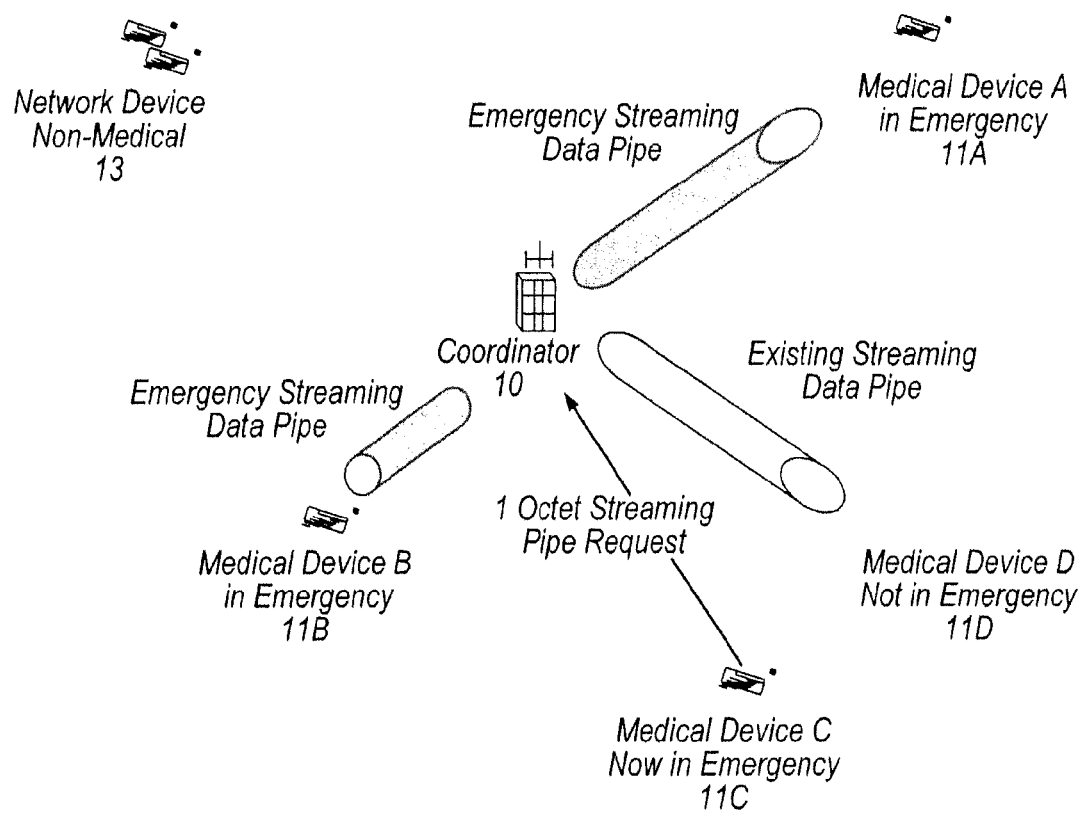

Now consider a situation where even more medical devices 11C go in emergency and require a streaming data pipe, as shown in FIG. 17.

Figure 18:
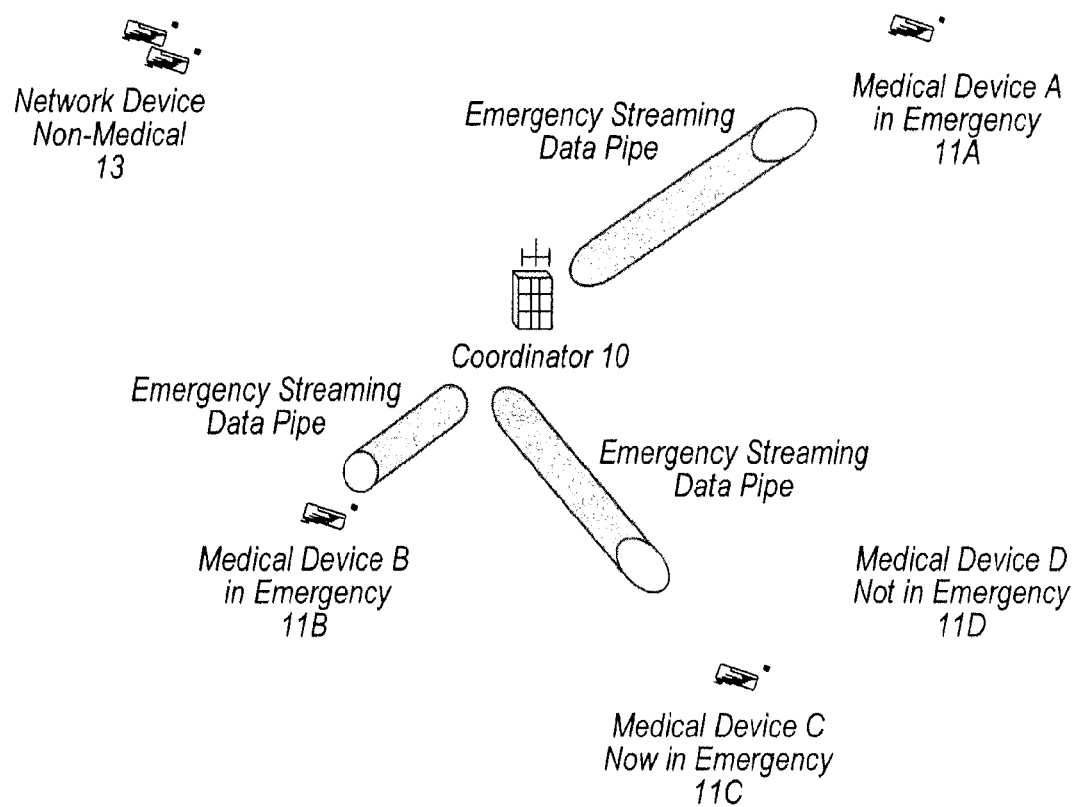

The coordinator follows a similar procedure to that described above. If there is no longer any non-medical pipe to be stopped, the coordinator turns to any medical devices not in emergency and asks them to temporarily give up their streaming data pipe to accommodate the new devices in emergency. Here "ask" may involve a request (or command) sent by the coordinator to the devices concerned; the coordinator might simply cut off the streams to those devices without needing permission, but it is preferable for the coordinator to notify the affected devices to maintain coordination in the network and avoid data loss. As shown in FIG. 18, the data pipe is allocated to the new device in emergency.

Figure 19:
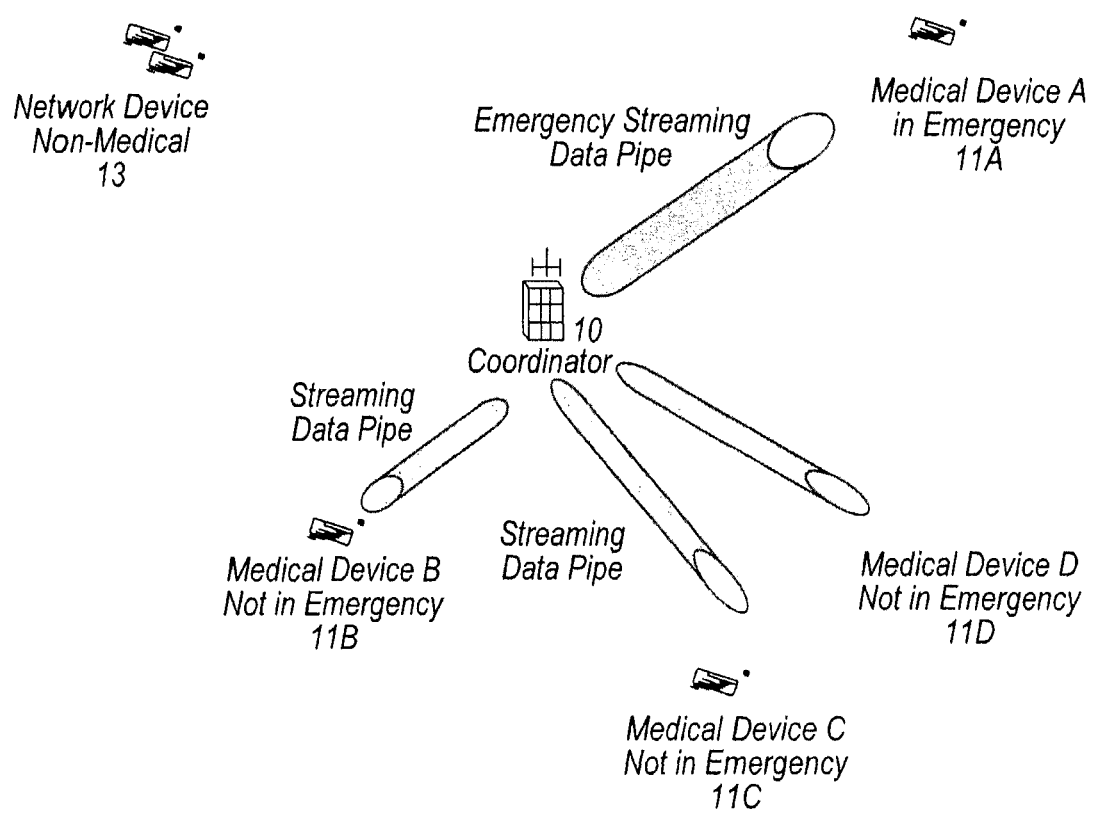

It may be expected that an emergency condition of one or more parameters sensed by the network is only of temporary duration. For example, in the case of medical monitoring, once the emergency condition has been signalled and the relevant parameter closely observed for a period by a network device, a patient could be attended to by medical staff in order to stabilise their condition. Or, in the case of monitoring a industrial installation, some action could be taken to rectify the cause of the emergency. When the emergency is lifted, the devices can come back to some different pipe arrangement as shown in FIG. 19. It can be seen that the medical devices 11B and 11C came out of emergency and the available data pipe is divided between them. They receive a smaller pipe in terms of diameter (i.e. smaller bit rates).

Figure 20A:
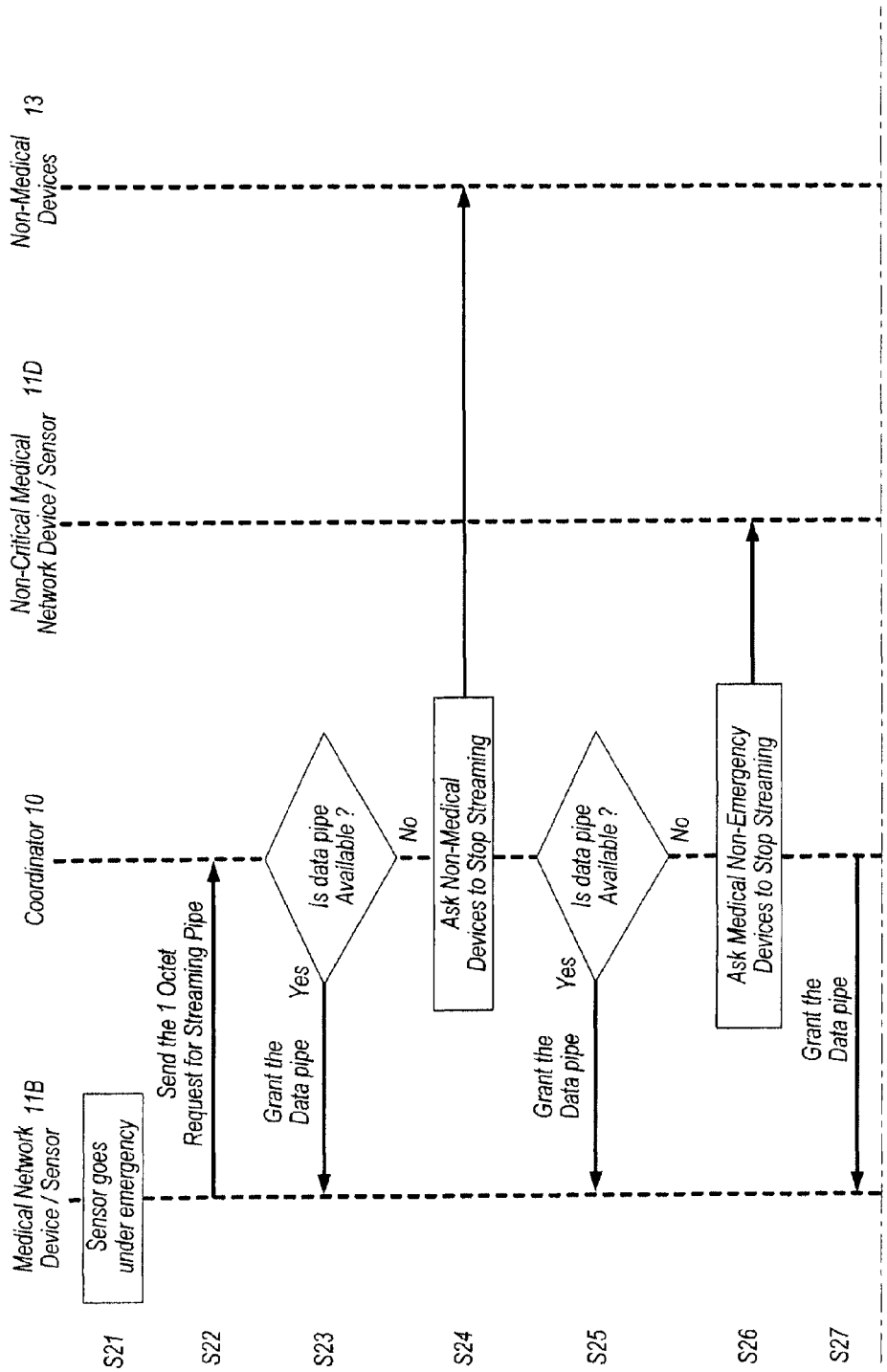
FIG. 20 is a flowchart for procedures according to an embodiment of the present invention for scheduling streams in an emergency or non-emergency situation respectively.
Figure 20B:
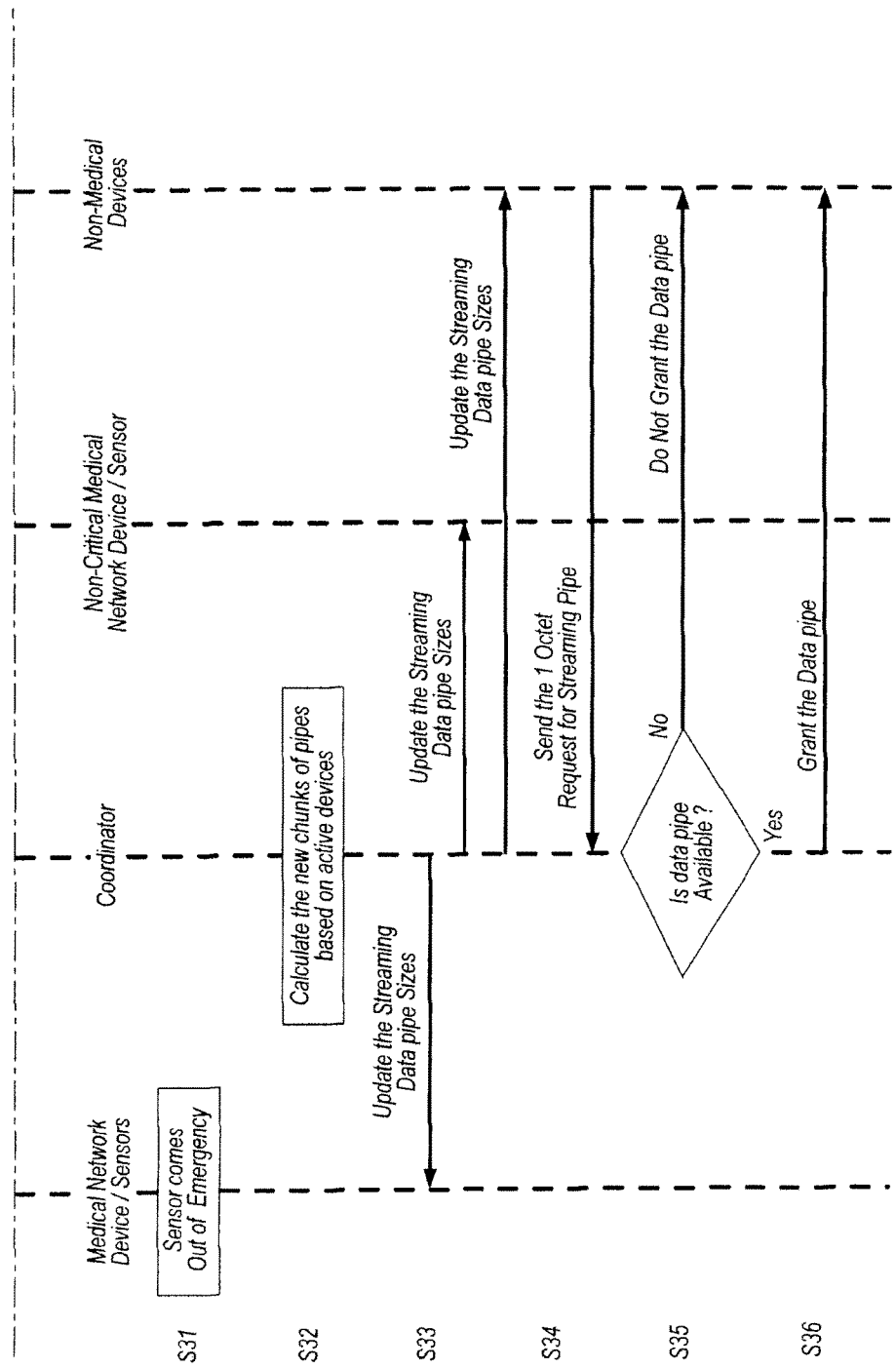

FIG. 20 describes the detailed signalling protocol for proposed emergency applications. The flowchart is in two parts: the upper half (steps S21 to S27) concerns actions taken in response to a new emergency condition, and the lower half (S31 to S36) concerns the procedure upon lifting of an emergency.

To begin with, suppose that a medical network device 11B (also referred to here simply as a sensor) goes under emergency (S21). This means, as already noted, that some parameter being sensed by the network device has reached some kind of critical value. From now on the network device concerned is said to be "in emergency".

At step S22, the network device 11B in emergency sends a streaming request to the coordinator 10. This request may be in the form of a one-octet long subfield in a frame header, assuming a frame-based system such as IEEE 802.15.4 outlined earlier.

At step S23, the coordinator 10 considers whether enough resources are available and if so, simply grants the required allocation. If No, i.e. there are not enough free resources to grant the request immediately, the coordinator 10 asks one or more non-medical devices 13 to stop streaming. The coordinator may wait for some form of acknowledgement from the non-medical device(s) 13 before proceeding further.

Then, in step S25, the coordinator 10 again checks whether sufficient resources are available. If the answer is now Yes, the data pipe for network device 11B is granted. If the answer is still No, i.e. if terminating the non-medical stream(s) has not freed up enough resources, the coordinator 10 sends (S26) a request/command to stop streaming to one or more medical devices 11D which are not currently in emergency, Finally, (S27) the coordinator grants the requested streaming allocation to device 11B.

Assume that after some time the device 11B finds itself (step S31) no longer in an emergency condition, in other words "comes out" of emergency. The coordinator 10 becomes aware of this fact in some way. For example, it may be the coordinator which decides whether or not each network device is in emergency, as each network device (sensor) may be too simple to decide this for themselves. Alternatively, the coordinator 10 may receive a notification either from the network device 11B itself or from a higher level control unit. Then (S32) the coordinator calculates how to re-allocate the resources no longer required by device 11B. In step S33, the coordinator 10 sends notifications (e.g., command frames) to each of the devices 11B, 11D and 13 of the updated streaming pipe sizes. In doing so, the coordinator will take into account the priority levels determined using the table of FIG. 10 and flowchart of FIG. 11.

Suppose that, in step S34, some other non-medical device 13 makes a new request for a streaming allocation. The coordinator 10 determines (S35) whether sufficient free resources are available and if No, does not grant the data pipe (since non-medical devices are considered to be of lowest priority, such that there is no need to change existing allocations to medical devices in or out of emergency). If Yes in S35, however, the coordinator grants the requested allocation (S36).

FIG. 21 illustrates a frame format 42' (MAC layer only) which generally corresponds to the IEEE 802.15.4 frame format 42 shown in FIG. 9. This format is one possible modification to the IEEE802.15.4 frame format to accommodate different types of QoS and make it suitable for IEEE802.15.6. A newly-defined one-Octet streaming index 52 is responsible for carrying the signalling information related to the nature of data streaming and the required bit rate. The stream index 52 may take values as shown in the following Table:

| Stream index (hexadecimal) | Data Stream Type Description | QoS |
| --- | --- | --- |
| 0x00 | Reserved for unassigned streams | N/A |
| 0x01-0x20 | For medical streams, where the BAN device is in a state of emergency. Or for non-medical device in emergency (e.g. Fire alarm or other home security signals) | Lowest possible delay in response to the required delay Highest available data rate pipe in response to the required bit rate Highest streaming priority |
| 0x21-0xC8 | For medical streams, where the BAN device is not in a state of emergency. | Required delay if possible Required data rate pipe if available Medium streaming priority |
| 0xC9-0xFF | For non-medical streaming not in state of emergency | Required delay if possible Required data rate pipe if available Lowest streaming priority |

Note that the above table allows for the possibility that non-medical devices may also be in emergency, in addition to medical devices. Here, the network device sends a request with stream index set to any value in the table to the coordinator. If the stream index is set to the value 0x00 this means that the device requests a new stream. The coordinator also receives indication of emergency condition (i.e. emergency bit). Then, based on its available resources, the coordinator assigns the stream index to any of the values in the same table back to the originating device. If the assigned stream index value is set to 0x00 this means the coordinator did not allocate resource to the originating device. Other values are interpreted according to the table.

On the assumption that the device has already established a stream, the device will send a stream index set to any value in the table except for 0x00. In this case, the stream index in the request originated from the device to the coordinator means that the device wants to modify the existing stream. If coordinator sends a stream index set to 0x00 this means that the coordinator termination of the stream.

In other words, each stream is given a number (the stream index) and by the range in which this number is set, the coordinator determines what type the stream is. The reserved field 0x00 is for unassigned streams and will be used by a network device to request from the coordinator the creation of a new isochronous stream. Network devices use other values of the stream index as dynamically assigned by the coordinator during the setup of the data stream, and as shown in the above Table. The coordinator allocates a unique stream index value for each isochronous stream in the BAN. By re-assigning stream indexes, the coordinator can re-allocate resources in the manner explained above with respect to FIGS. 12 to 19.

As a further technique for integrating the novel features of the present invention into frame structures already proposed, the command frame identifier of a MAC command frame (refer back to FIG. 9B) may be used. Recalling that the MAC command frame includes a command frame identifier field 440, FIG. 22 shows the addition of new frame identifiers 0x0c for Channel Time Request and 0x0d for Channel Time Response, using two bit values which are reserved in the IEEE 802.15.4 specification.

In order for a device to request a stream from a coordinator, the additional MAC command, called Channel Time Request (CTRq) similar to that provided in IEEE 802.15.3, is introduced to the table of MAC command frames of 15.4. The coordinator will respond to that request using a Channel Time Response as a MAC command frame, introduced from 15.3.

The above protocols only involve the sensor and the coordinator. However, an MBAN may be implemented in such a way that several coordinators report to some form of central monitor as previously mentioned, which could be either automatic or under human supervision. For example, such a central monitor could be located at the desk of a ward sister who oversees several patients in a hospital. In this scenario, data transfers to and from the central monitor and pertaining to the network device in emergency (for example, sensed data from a network device in emergency, which the coordinator relays to the central monitor) can also be streamed in the same way. In addition, as already mentioned, such a central monitor could assist (or even take over) the scheduling task of the coordinator.

Although the above description has referred only to sensors and coordinators in a wireless sensor network, with the possible inclusion of a central monitor, it is possible for a MBAN to include other devices than these kinds. Potentially, some means of intervening in a patient's care, such as a drug dispensing mechanism or other actuator device, could be arranged in the network under wireless control of the coordinator and/or any central monitor. Thus, the streaming enabled by the present invention is not confined to sensor data but could be a stream of control values from a coordinator to such an actuator device, for example to deliver a drug to the patient to stabilise a life parameter like heart rate.

Typically, the emergency condition referred to above will be a medical condition of a patient, since this is seen as an important application of the present invention. However, it is not the only possible application. Sensors could be used to monitor living bodies in non-medical situations. For example, any person at risk (examples: old or frail people, or children; people in dangerous environments, etc.) could be monitored using a BAN of sensors. In this case, the emergency condition would represent some form of physical threat such as an accident, and streaming could again be employed to improve reliability of communications with sensors relevant to monitoring the emergency. For example, the stream could contain real-time video from a camera worn on the living body.

Moreover, the present invention is not confined to use on living bodies. There are many possibilities beyond the BAN human or other living body. One possibility is a WSN capable of detecting industrial emergencies such as many potential scenarios in a mission critical industrial environment (for example, power stations). This can apply to multiple control points in a factory environment. For example we may consider temperature sensors in a factory's heating facility or pressure thresholds for food product lines. In addition, as mentioned, non-medical devices could be use for safety and security purposes, declaring an emergency for example on detecting smoke or intrusion of a person into a secure area. The above streaming and QoS measures may applied to emergencies in these systems just as for medical emergencies. Thus, the term "entity" in the claims is to be interpreted as covering any such industrial environment in addition to a living being.

Thus, an embodiment of the present invention may have any of the following features:—

Involving status of emergency in scheduling of streaming sequences and their allocated data rates (i.e. how fat the data pipe is).

A priority based novel scheduling mechanism specially designed to schedule the streaming data pipes in presence of non-medical applications and non-emergency medical applications.

A new request mechanism for streaming data which make the top priority handling of emergency medical applications a possibility.

A related novel control frame structure for IEEE 802.15.6 by introducing a new streaming request field for IEEE 802.15.4.

Potential Mapping of QoS of Streaming to the Nature of Application (Medical or Non-Medical) and Potential Emergency Relying on three Classes of Data Rates and Delays.

Concept of slowing down and even temporarily stopping the non-medical streaming when emergency streaming data is present.

INDUSTRIAL APPLICABILITY

Embodiments of the present invention may provide one or more of the following advantages:
(a) Many emerging wireless sensor medical applications have the potential for data streaming. Streaming of medical data especially in emergencies is a challenging task. Current patent proposal guarantees a safe data pipe provisioning under emergency. The proposed streaming scheduling mechanisms makes sure that a fair division of available data rates between emergency and non-emergency medical services is possible.
(b) The proposed scheduling mechanisms are dynamic meaning that in response to the lifting emergency conditions the streaming of non-emergency streaming may be resumed or go back to higher data rate providing a fair allocation of resources considering the severity of medical situation.
(c) Avoiding poor quality of streaming data for highly critical emergency applications, reducing human error, and potentially saving the lives of patients who may go under emergency conditions.
(d) Improving the labour costs and efficiency of emergency response in a medical system.
(e) Improving the emergency awareness in a medical MBAN system by facilitating reliable transmission of sensor data from sensors in emergency.

Embodiments of the present invention may have a vital role to play in facilitating emergency management by use of MBANs. The following scenarios may be noted:
(i) Hundreds of millions of patients worldwide with cardiac and heart problems can be monitored in hospital or at home by employing wireless sensors forming an MBAN on their bodies. The MBAN can provide extra mobility for such patients. However, for this group of patients under situations such as abnormal heart functioning or more severe cases such as heart attack, it is vital to secure a reliable communication channel to make sure that no emergency or alarm signal will be missed. The present invention provides a secure emergency trigger mechanism to make all the entities involved aware about an emergency by sending an immediate ACK or "Emergency Acknowledge".
(ii) Hundreds of millions of people worldwide suffer from diabetes. Implantable or non-invasive methods for glucose measurement have been considered recently. An MBAN can be used to monitor a patient's glucose level information on a 24-hour basis. There are situations where the patient's glucose level is off the chart and emergency geolocation and other necessary urgent medical procedures for the patients are required.
(iii) MBANs may be used to gather sensed data while monitoring a patient in intensive care where the loss of data could be life threatening.
(iv) Improves the labour costs and efficiency of emergency response in a medical system.
(v) Improves the emergency awareness in a medical MBAN system.
(vi) Reduces the labour costs by automating the emergency response process.
(vii) Although primarily envisaged for low data-rate applications, MBANs could have application to transfer of streaming video/audio data where loss of individual packet is crucial and affects the quality. Erroneous data may have a negative impact on the diagnosis of illness in emergency cases.
(viii) For medical diagnosis, MMR or X-ray images need to be very clear in order for the doctor to diagnose properly the patient. Again, therefore, reliable data transfer is essential.

In summary, the present invention can provide a technique for allocating resources in a wireless sensor network, the network having functions including medical monitoring of a patient using multiple network devices having sensors, the method including steps of: sensing, by a network device in the network, a life parameter of the patient; recognising the existence of an emergency condition with respect to the parameter; the network device sending a request for streaming towards a coordinator of the network; the coordinator receiving (S12) the request along with any other requests from other devices in the network; and the coordinator granting (S14, S16) each the request by scheduling one of: a streaming allocation with highest priority for a network device which is in an emergency condition; a streaming allocation of medium priority for a network device sensing a life parameter which is not in an emergency condition; and a streaming allocation of lowest priority for a network device which is not sensing any life parameter of the patient and which is not in an emergency condition. The emergency condition may be defined with respect to one or more medical parameters of the patient. The method may be applied, for example, to monitoring of patients in a hospital using MBANs operating in accordance with IEEE 802.15.6.

The present invention may take the form of a novel sensor, coordinator, or hardware modules for the same, and can be implemented by replacing or modifying software executed by processors of the sensor(s) and/or the coordinator.

Thus, embodiments of the present invention may be implemented in hardware, or as software modules running on one or more processors, or on a combination thereof. The invention may also be embodied as one or more device or apparatus programs (e.g. computer programs and computer program products) for carrying out part or all of any of the techniques described herein. Such programs embodying the present invention may be stored on computer-readable media, or could, for example, be in the form of one or more signals. Such signals may be data signals downloadable from an Internet website, or provided on a carrier signal, or in any other form.

Although the above description has referred to IEEE 802.15.4 and IEEE 802.15.6 by way of example, the invention may be applied to any type of frame-based wireless sensor network or MBAN whether or not operating in accordance with IEEE 802.15.6, as well as to other types of BAN which even if not medical body area networks nevertheless have a requirement for improved reliability of communication in emergency situations.

The invention claimed is:
1. A coordinator for use together with other network devices in a wireless sensor network, including:

transceiver means arranged to receive a request for streaming originated by at least one of the network devices; and scheduling means arranged to grant the request by allocation of network resources to an extent determined by conditions in the network, said conditions including whether the network device which originated the request is a medical device, and whether the network device which originated the request is a medical device in an emergency condition involving a life-threatening medical emergency in respect of a life parameter being sensed by a sensor of the medical device from which the request originated, wherein the scheduling means is arranged to grant the request by scheduling any of the following types of streaming allocation within a contention-free period:

a streaming allocation with highest priority for a medical device in a said emergency condition;

a streaming allocation of medium priority for a medical device not in a said emergency condition; and a streaming allocation of lowest priority for a non-medical device, wherein priority of a streaming allocation determines the size of a data pipe to or from the network device.

2. The coordinator according to claim 1 wherein the scheduling means is responsive to a declaration of the emergency condition received in said request or received independently by other means.

3. The coordinator according to claim 1, arranged for wireless communication with said network devices in units of frames, wherein upon receipt of a frame containing a said request by the transceiver means, the scheduling means is responsive to a streaming request included in a frame header.

4. The coordinator according to claim 3 wherein the scheduling means is arranged to set a stream index indicating the type of streaming allocation being requested and the transceiver means is arranged to transmit a frame containing the stream index in its frame header.

5. The coordinator according to claim 1 wherein the scheduling means is further arranged for taking away network resources allocated to an existing stream in the network if necessary to grant the request originated from a medical device in a said emergency condition.

6. The coordinator according to claim 1 wherein the scheduling means is further arranged, in response to a said medical device lifting its emergency condition, to re-allocate, to other network devices, resources which had been allocated to a stream requested by that medical device.

7. A wireless sensor network including at least one coordinator according to any of claims 1 to 5 and a plurality of network devices each comprising a sensor for sensing a life parameter of a patient monitored by the network;

emergency recognizing means for recognizing an emergency condition involving a life-threatening medical emergency in respect of the life parameter being sensed by the sensor; and requesting means responsive to the recognizing means recognizing a said emergency condition to transmit a request for streaming towards the coordinator.

8. A method of allocating resources in a wireless sensor network, the network comprising network devices and having functions including medical monitoring of a patient using multiple medical devices having sensors among said network devices, the method including steps of:

sensing, by a medical device in the network, a life parameter of the patient;

recognizing the existence of an emergency condition involving a life-threatening medical emergency in respect of the life parameter being sensed by the sensor;

said medical device sending a request for streaming towards a coordinator of the network;

said coordinator receiving said request along with any other requests from other network devices; and said coordinator granting each said request by scheduling one of the following types of streaming allocation within a contention-free period:

a streaming allocation with highest priority for a medical device sensing a life parameter which is in a said emergency condition;

a streaming allocation of medium priority for a medical device sensing a life parameter which is not in an emergency condition; and a streaming allocation of lowest priority for a network device which is not a medical device, wherein priority of a streaming allocation determines the size of a data pipe to or from the network device.

* * * * *

UNITED STATES PATENT AND TRADEMARK OFFICE
CERTIFICATE OF CORRECTION

PATENT NO. : 9,681,492 B2
APPLICATION NO. : 13/254069
DATED : June 13, 2017
INVENTOR(S) : Saied Abedi et al.

Page 1 of 1

It is certified that error appears in the above-identified patent and that said Letters Patent is hereby corrected as shown below:

On the Title Page

Item [54] and in the Specification, Column 1 (Title):
Delete "IMPROVEMENTS WIRELESS SENSOR NETWORKS" and insert
-- IMPROVEMENTS TO WIRELESS SENSOR NETWORKS --, therefore.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*